United States Patent
Schecter

(10) Patent No.: US 10,886,011 B2
(45) Date of Patent: Jan. 5, 2021

(54) SYSTEMS AND METHODS FOR OPTIMIZING MANAGEMENT OF PATIENTS WITH MEDICAL DEVICES AND MONITORING COMPLIANCE

(71) Applicant: Icahn School of Medicine at Mount Sinai, New York, NY (US)

(72) Inventor: Stuart Owen Schecter, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/780,890

(22) PCT Filed: Dec. 2, 2016

(86) PCT No.: PCT/US2016/064716
§ 371 (c)(1),
(2) Date: Jun. 1, 2018

(87) PCT Pub. No.: WO2017/096224
PCT Pub. Date: Jun. 8, 2017

(65) Prior Publication Data
US 2018/0358114 A1 Dec. 13, 2018

Related U.S. Application Data

(60) Provisional application No. 62/386,452, filed on Dec. 2, 2015.

(51) Int. Cl.
*G16H 10/60* (2018.01)
*G06Q 50/22* (2018.01)
(Continued)

(52) U.S. Cl.
CPC ............ *G16H 10/60* (2018.01); *G06Q 30/018* (2013.01); *G06Q 50/22* (2013.01); *A61B 5/0022* (2013.01); *A61B 5/0031* (2013.01); *A61B 5/7275* (2013.01)

(58) Field of Classification Search
None
See application file for complete search history.

(56) References Cited

U.S. PATENT DOCUMENTS 8,818,522 B2 * 8/2014 Mass ................ G06Q 50/24
607/60
8,827,904 B2 * 9/2014 Ball ................... A61B 5/0002
600/300

(Continued)

OTHER PUBLICATIONS

Medtronic 2010 CPT Codes for Cardiac Monitoring (pamphlet), 8 pages.

(Continued)

*Primary Examiner* — Michael Tomaszewski
(74) *Attorney, Agent, or Firm* — Morgan, Lewis & Bockius LLP

(57) ABSTRACT

Systems and methods for determining monitoring compliance are provided. Each element in a plurality of data elements is obtained from a medical device connected to a corresponding subject in a first plurality of subjects and interrogated to determine a condition of the device or subject. A medical code and timestamp for evaluation of the device or subject is recorded in the subject's medical record. A determination is made for each epoch in a plurality of epochs, for each subject in a second plurality of subjects, whether the medical code is recorded in the subject's medical record for the epoch by evaluating the time stamps and codes in the medical records. A compliance counter is advanced when a medical record includes the code for a respective epoch and otherwise a noncompliance counter is (Continued)

advanced. Responsive to a compliance request, compliance information or suggested treatment options are provided based on the counters.

45 Claims, 18 Drawing Sheets

(51) Int. Cl.
  *G06Q 30/00* (2012.01)
  *A61B 5/00* (2006.01)

(56) References Cited

U.S. PATENT DOCUMENTS

| | | | |
|---|---|---|---|
| 2008/0086327 A1* | 4/2008 | Cox | G06Q 10/00 705/2 |
| 2009/0058635 A1 | 3/2009 | LaLonde et al. | |
| 2010/0036253 A1* | 2/2010 | Vezina | A61B 8/5292 600/453 |
| 2012/0330685 A1* | 12/2012 | Hasan | G06F 19/328 705/3 |
| 2014/0032232 A1* | 1/2014 | Brown | G06Q 50/22 705/2 |
| 2014/0278473 A1* | 9/2014 | Duff | G16H 40/67 705/2 |
| 2016/0310077 A1* | 10/2016 | Hunter | A61B 5/686 |

OTHER PUBLICATIONS

Akar et al., "Use of Remote Monitoring of Newly Implanted Cardioverter-Defibrillators," Circulation, 2013, 16 pages.

International Search Report and Written Opinion for International Patent Application No. PCT/US2016/064716, dated Mar. 23, 2017, 10 pages.

EPO Communication with Supplementary European Search Report for European Patent Application No. 16871614.0, dated May 10, 2019, 9 pages.

Mittal et al., "Performance of a remote interrogation system for the in-hospital evaluation of cardiac implantable electronic devices", *J Interv Card Electrophysiol*, Aug. 2016;, 46(2), pp. 121-128. Epub Dec. 22, 2015.

* cited by examiner

426 — In the first autonomous process, responsive to the interrogating, there is recorded (a) a first medical code that indicates that the condition of the medical device or the condition of the corresponding subject has been evaluated and (b) an associated timestamp for the interrogating is recorded in a medical record associated with the corresponding subject.

428 — The first medical code is an ICD-9 code, an ICD-10 code, a Current Procedure Terminology (CPT) code, or an equivalent thereof.

432 — The medical record is an electronic medical record.

434 — The first medical code is a Current Procedure Terminology (CPT) code 93294, 93295, 93296, 93297, 93298, 93299, 93279, 93280, 93281, 93282, 93283, 93284, 93285, 93288, 93289, 93290 or an equivalent thereof 436 — The first medical code is representative of one or more of an in office interrogation, reprogramming, fitting or adjustment of the corresponding medical device or a remote monitoring evaluation of the corresponding medical device.

438 — The first medical code is an ICD-10 code is Z95.0, Z45.018, Z95.810, Z45.02, or an equivalent thereof.

440 — The first medical code is a ICD-10 code I63.4, I63.40, I63.41, I63.411, I63.412, I63.413, I63.419, I63.42, I63.421, I63.422, I63.423, I63.429, I63.43, I63.431, I63.432, I63.433, I63.439, I63.44, I63.441, I63.442, I63.443, I63.449, I63.49, I63.1, I63.10, I63.11, I63.111, I63.112, I63.113, I63.119, I63.12, I63.13, I63.131, I63.132, I63.133, I63.139, I63.19, I63.9, or an equivalent thereof.

Fig. 4C

442 — The second autonomous process is performed at each respective epoch in a plurality of epochs and comprises, for each respective subject in a second plurality of subjects, a determination as to whether the first medical code has been recorded in the medical record associated with the respective subject during the respective epoch. This is done by parsing the medical record for the first medical code and, when found in the medical record, using the associated timestamp to determine if the first medical code is associated with respective epoch. The first plurality of subjects constitutes all or a portion of the second plurality of subjects. Each subject in the second plurality of subjects has a corresponding medical device.

443 — The first medical code is extracted from the context of the medical record thereby providing semantic interoperability without specific reliance on a coding standard.

444 — Each corresponding medical device is a pacemaker. The second autonomous process further comprises identifying the second plurality of subjects by scanning the medical record associated with each subject in a third plurality of subjects for a second code. The second plurality of subjects is all or a portion of the third plurality of subjects. The second code is ICD-10 Z95.0, ICD-10 Z45.018, CPT 93279, CPT 93280, or CPT 93281. The first code is CPT 93294 or CPT 93296.

446 — Each corresponding medical device is a defibrillator. The second autonomous process further comprises identifying the second plurality of subjects by scanning the medical record associated with each subject in a third plurality of subjects for a second code. The second plurality of subjects is all or a portion of the third plurality of subjects. The second code is ICD-10 Z95.810, Z45.02, CPT 93282, CPT 93283, or 93284. The first code is CPT 93295 or 93296.

448 — The interrogating the data element in the first autonomous process determines the condition of the corresponding subject, where the condition is an index of cardiorespiratory function, and each respective epoch in the plurality of epochs is a day.

450 — Each respective epoch in the plurality of epochs is the same length of time, and wherein the length of time is an hour or less, a day or less, two days or less, a week or less, a month or less, or a quarter of a year or less.

452 — The first autonomous process and the second autonomous process occur concurrently.

> The second plurality of subjects is associated with a physician, a provider group, a hospital, a hospital network, a health insurance company, a pharmacy, a governmental body, or a prescribing clinician.

456

> The second plurality of subjects is associated with a physician, a provider group, a hospital, a hospital network, a health insurance company, a pharmacy, a governmental body or a prescribing clinician. Each subject in the second plurality of subjects has a pathologic condition (e.g., cardiomyopathy, congestive heart failure, arrhythmia, a cardiorespiratory impairment, or a neurologic ailment). The interrogating the data element in the first autonomous process determines a condition of the medical device. The corresponding medical device of the corresponding subject wirelessly transmits the respective data element.

458

> The second plurality of subjects is associated with a physician, a provider group, a hospital, a hospital network, a health insurance company, a pharmacy, a governmental body, or a prescribing clinician. Each subject in the plurality of subjects has cardiomyopathy or congestive heart failure. The interrogating the data element in the first autonomous process determines the condition of the corresponding subject. The condition is a pathologic condition (e.g., cardiomyopathy, congestive heart failure, arrhythmia, a cardiorespiratory impairment, or a neurologic ailment). The corresponding medical device of the corresponding subject wirelessly transmits the respective data element.

460

> The second plurality of subjects is associated with a physician, a provider group, a hospital, a hospital network, a health insurance company, a pharmacy, a governmental body, or a prescribing clinician. Each subject in the second plurality of subjects has been diagnosed with an ailment. Each subject in the second plurality of subjects has been coded for hospital readmission for the ailment.

462 — The second plurality of subjects is associated with a physician, a provider group, a hospital, a hospital network, a health insurance company, a pharmacy, a governmental body, or a prescribing clinician. Each subject in the second plurality of subjects satisfies a set of screening criteria.

464 — The set of screening criteria comprises (i) historical tobacco use, (ii) male, and (iii) over 65 years of age. The interrogating the data element in the first autonomous process determines a condition of the corresponding subject. The condition is whether a predetermined treatment regimen has been performed on the corresponding subject.

466 — The set of screening criteria comprises 2, 3, 4, 5, 6, 7, 8, 9, 10, or more criteria. The interrogating the data element in the first autonomous process determines a condition of the corresponding subject. The condition is whether a predetermined treatment regimen has been performed on the corresponding subject.

468 — The second autonomous process further comprises identifying the second plurality of subjects by scanning the medical record associated with each subject in a third plurality of subjects for a second code. The second plurality of subjects is all or a portion of the third plurality of subjects. The second code is ICD-10 I44.7, ICD-10 Z95.810, CPT 93282, or CPT 93283. The first code is CPT 93284.

470 — The second autonomous process further comprises identifying the second plurality of subjects by scanning the medical record associated with each subject in a third plurality of subjects for a second code. The second plurality of subjects is all or a portion of the third plurality of subjects. The second code is a combination of a first CPT code or ICD-10 code, or equivalent thereof, identifying that a subject has an implanted cardiac rhythm management device that does not include cardiac resynchronization therapy and a second CPT or second ICD-10 code, or equivalent thereof, identifying the patient as having congestive heart failure or risk for congestive heart failure.

472 — The first CPT code or ICD-10 code is ICD-10 Z95.0, ICD-10 Z45.018, ICD-10 Z45.02 or ICD-10 Z95.810. The second CPT code or ICD-10 code is ICD-10 I44.7, ICD-10 I44.2, ICD-10 I44.3, ICD-10 I50.22, ICD-10 I50.23, ICD-10 I50.32, ICD-10 I50.42, ICD-10 I50.43, or ICD-10 I50.20.

446 (cont)
474

The second autonomous process further comprises identifying the second plurality of subjects by scanning the medical record associated with each subject in a third plurality of subjects for a second code. The second plurality of subjects is all or a portion of the third plurality of subjects. The second code is a CPT code identifies the patient as having cardiac resynchronization therapy.

476

The CPT code is 93281 or 93284.

478

The second autonomous process further comprises identifying the second plurality of subjects by scanning the medical record associated with each subject in a third plurality of subjects for a second code. The second plurality of subjects is all or a portion of the third plurality of subjects. The second code is an ICD-10 code, or equivalent thereof, identifying the patient as having cardiac resynchronization therapy.

480

The ICD-10 code is in the I44.x or I50.yy families of ICD-10 codes, or is an equivalent thereof.

482

Each corresponding medical device is an implantable loop recorder. The second autonomous process further comprises identifying the second plurality of subjects by scanning the medical record associated with each subject in a third plurality of subjects for a second code. The second plurality of subjects is all or a portion of the third plurality of subjects. The second code is a second CPT-10 code, or equivalent thereof, that identifies a corresponding subject as having an implantable loop recorder evaluated in the office. The first code is a first CPT-10 code, or equivalent thereof, that identifies whether or not the corresponding subject's implantable loop recorder is being monitored remotely at specific time intervals.

484

The first code is CPT-10 93298 or 93299 and the second code is CPT-10 92385.

486

Each corresponding medical device is an implantable loop recorder. The second autonomous process identifies the second plurality of subjects by scanning the medical record associated with each subject in a third plurality of subjects for a second code. The second plurality of subjects is all or a portion of the third plurality of subjects. The second code is within the family of ICD-10 I63.4, ICD-10 I63.1, or I63.9, or equivalent thereof. The first code is CPT 93285 or CPT 93298.

488

The first code is CPT-10 93298 or 93299 and the second code is CPT-10 92385.

Fig. 4G

```
                                                   496 (cont)
                                                   502
┌─────────────────────────────────────────────────────┐
│ ┌─────────────────────────────────────────────────┐ │
│ │ The second autonomous process further comprises determining whether │ │
│ │ each subject in the plurality of subjects has been prescribed a medication by │ │
│ │ parsing the medical record associated with each subject in the second │ │
│ │ plurality of subjects for an indication of the medication. The medication is │ │
│ │ for a beta blocker, a lipid lowering therapy, an angiotensin converting │ │
│ │ enzyme inhibitor, an angiotensin receptor blocker, an aldosterone receptor │ │
│ │ blocker, hydralazine, a nitrate, a PCSK9 inhibitor, a negative chronotropic │ │
│ │ agent, a hyperpolarization-activated cyclic nucleotide-gated channel │ │
│ │ blocker, an anti-platelet agent, an anti-coagulant, a Neprilysin inhibitor, or a │ │
│ │ cardiac sinus node inhibitor.                                                  504
│ │   ┌─────────────────────────────────────────────┐ │ │
│ │   │ The presence of the indication of the medication in the medical │ │ │
│ │   │ records corresponding to the second plurality of subjects contributes to │ │ │
│ │   │ the compliance information.                 │ │ │
│ │   └─────────────────────────────────────────────┘ │ │
│ └─────────────────────────────────────────────────┘ │
│                                                   506
│ ┌─────────────────────────────────────────────────┐ │
│ │ The second autonomous process further comprises determining whether │ │
│ │ each subject in the second plurality of subjects has been prescribed a │ │
│ │ supplemental medical device by parsing the medical record associated with │ │
│ │ each subject in the second plurality of subjects for a second medical code. │ │
│ │ The supplemental medical device is a cardiac rhythm management device, a │ │
│ │ cardiac rhythm management device configured to monitor or treat │ │
│ │ congestive heart failure, a heart failure treatment device, a respiratory │ │
│ │ support apparatus, a non-invasive ventilation therapy, or a continuous │ │
│ │ positive airway pressure device.                                               508
│ │   ┌─────────────────────────────────────────────┐ │ │
│ │   │ The presence of the second medical code in the medical records │ │ │
│ │   │ corresponding to the second plurality of subjects contributes to the │ │ │
│ │   │ compliance information.                     │ │ │
│ │   └─────────────────────────────────────────────┘ │ │
│ └─────────────────────────────────────────────────┘ │
│                                                   510
│ ┌─────────────────────────────────────────────────┐ │
│ │ The second autonomous process further comprises determining whether │ │
│ │ each subject in the second plurality of subjects has been prescribed a │ │
│ │ supplemental therapy by parsing the medical record associated with each │ │
│ │ subject in the second plurality of subjects for a second medical code. The │ │
│ │ supplemental therapy is non-invasive ventilation therapy.                      512
│ │   ┌─────────────────────────────────────────────┐ │ │
│ │   │ The presence of the second medical code in the medical records │ │ │
│ │   │ corresponding to the second plurality of subjects contributes to the │ │ │
│ │   │ compliance information.                     │ │ │
│ │   └─────────────────────────────────────────────┘ │ │
│ └─────────────────────────────────────────────────┘ │
└─────────────────────────────────────────────────────┘
```

514
The third process identifies the absence of an expected treatment or diagnostic modality or provides a suggested treatment for a subject in the first plurality of subjects when the compliance information indicates that treatment for the subject has failed a compliance threshold over the plurality of epochs.

516
The third process identifies the absence of an expected treatment or diagnostic modality, or provides a suggested treatment for a subset of subjects in the first plurality of subjects when the compliance information indicates that treatment for the subset of subjects has failed a compliance threshold over the plurality of epochs.

518
The respective data element in the plurality of data elements from the corresponding medical device provides a condition of the subject that is recorded in the medical record associated with the subject and the third process provides a suggested treatment for the subject based upon the condition or identifies the absence of an expected treatment or diagnostic modality.

520
The condition is an irregular heartbeat and the suggested treatment regimen is a medication for the irregular heartbeat.

522
The condition is a thoracic impedance measurement that indicates that the subject has congestive heart failure and the one or more suggested treatment options is to provide the subject with a device that provides resynchronization therapy or biventricular pacing when the subject's record indicate that they have not been provided with resynchronization therapy or biventricular pacing.

524
The compliance counter and the noncompliance counter are two separate counters.

526
The compliance counter and the noncompliance counter are a single counter.

Fig. 4J

SYSTEMS AND METHODS FOR OPTIMIZING MANAGEMENT OF PATIENTS WITH MEDICAL DEVICES AND MONITORING COMPLIANCE

CROSS REFERENCE TO RELATED APPLICATIONS

This Application is a National Stage of International Patent Application No. PCT/US2016/064716, entitled "Systems and Methods for Optimizing Management of Patients with Medical Devices and Monitoring Compliance," filed Dec. 2, 2016 and published as WO 2017/096224 A1, which claims priority to U.S. Patent Application No. 62/386,452 entitled "Method and algorithm for optimizing a health network's management of patients with cardiac implantable devices and monitoring compliance," filed Dec. 2, 2015, each of which is hereby incorporated by reference.

TECHNICAL FIELD

The present disclosure relates generally to systems and methods for monitoring medical or diagnostic devices to ascertain the status of the devices or the subjects to which they are associated.

BACKGROUND

Device management is an important component of health care. Devices, such as implanted devices in patients, need to be checked on a periodic basis to ascertain that they are in good working order. Moreover, as part of such checks, measurements of patient observables that the devices are uniquely capable of measuring can be retrieved. Thus, device management serves to not only ensure proper working order, but also serves as a means for monitoring patient health. The problem with device management is that service care providers often cannot negotiate favorable terms for the expense of device management from insurance companies or government medical programs. That is, the health codes under which a service care provider may seek reimbursement for evaluating the integrity of medical devices are often less than the actual costs for such evaluation. Related to this problem, there is often no organized or efficient means for evaluating whether a health care institution is checking such medical devices on a regular basis. A promising approach to such evaluation is remote management in which the medical devices remotely report on their status and provide measurements of patient observables measured by such devices.

One form of medical device evaluation is cardiac device remote monitoring, which refers to the monitoring of patients implanted with cardiac rhythm management ("CRM") devices and the monitoring of the implanted device's functionality. These cardiac implantable electronic devices ("CIED") include permanent pacemakers ("PPM"), implantable cardioverter defibrillators ("ICD"), cardiac resynchronization therapy devices ("CRT") and implantable loop recorders ("ILR"). CRT devices are used to treat and prevent congestive heart failure ("CHF") and can be either PPMs or ICDs that synchronize myocardial activation by providing multi-site pacing stimuli.

CIEDs are used to treat and/or diagnose cardiac rhythm disorders and are often monitored in the office and preferably remotely evaluated using Internet based applications provided by cardiac rhythm management vendors. PPMs are implanted for patients with a slow heart rate (bradycardia), ICDs are implanted to prevent cardiac arrest (ventricular tachycardia, ventricular fibrillation), CRT or biventricular devices are used to synchronize the electrical-mechanical activation of the heart, treat, diagnose and prevent congestive heart failure. ILRs are used to diagnose the cause of syncope, define the etiology of cryptogenic stroke, and identify arrhythmias such as atrial fibrillation. Modern CRM devices have means for identifying cardiac arrhythmia and most are capable of notifying the patient and/or physician of alert conditions. The alert conditions include arrhythmias that may cause sudden death, syncope with injury, stroke, and identify a device system malfunction. The device system comprises the actual device itself and leads (wiring) that are implanted within or about the heart. However, as used herein, the terms "device" and device system" are used interchangeably.

Remote management systems enable daily data transmissions, with minimal requisite patient interaction and can alert clinicians to arrhythmia events according to settings defined by clinicians. The ability of implanted CRM devices to identify and alert patients and physicians of adverse conditions has led medical experts to recommend that such devices be properly monitored by qualified medical personnel in order to improve patient outcome, reduce hospitalizations, and prolong survival. These efforts will translate into health care savings for patients, providers, and hospitals, and reduce the overall burden on the health care system.

Multiple trials in hundreds of thousands of patients have demonstrated that remote management enables early identification of cardiac arrhythmia, provides survival benefits, and reduces hospitalization for patients compliant with remote management. The ASSERT trial (Asymptomatic Atrial Fibrillation and Stroke Evaluation in Pacemaker Patients) (NEJM 2012) demonstrated that subclinical AF detected only by PPMs was associated with a 2.5 factor increase in stroke or systemic embolism. Patients with no prior history of AF subclinical atrial tachyarrhythmias are associated with a 2.49-fold increase risk of stroke or system embolism ($p=0.007$) and a 5.56-fold increase risk of clinical atrial fibrillation ($p<0.001$). The BRADYCARE Registry (Thankur et. al., Heart Rhythm Society 2013: PO04-10) demonstrated that remote monitoring was associated with a reduction in one-year mortality. Post-implant mortality after adjusting for co-morbidities was 3.9% for patients connected via remote monitoring vs. 8.3% for patients not enrolled.

The CONNECT trial (Crossley et al., The CONNECT "Clinical Evaluation of Remote Notification to Reduce Time to Clinical Decision" Trial; JACC. 2011; 57 (10):1181-1189, doi:10.1016/j.jacc.2010.12.012) concluded that when compared to standard in-office follow-up, remote monitoring with automatic alerts reduced time to clinical decision from 22 days to 4.6 days. Suboptimal compliance has been proven to undermine the ability of remote management to transmit data. In CONNECT 45% of clinician alerts were never transmitted "mainly because the home monitor was not set up and initiated to send out transmission."

Mittal et al. demonstrated that increased adherence to remote management using St. Jude Medical's Merlin RM system is associated with reduced mortality in patients implanted with CRM devices (Mittal et al. HRS 2014). The results of this study were presented at the International Heart Rhythm Society ("HRS") 2014 meeting, analyzed over 340,000 device patients and demonstrated that patients who were compliant with weekly remote transmissions over 75% of the time had a 2.23 times greater survival than patients who were not set up with remote monitoring. This was true for all device types and even for patients who were compliant with RM <75% of the time had 1.49 times greater survival than patients without RM. The PREDICt-RM study (Circulation. 2013 Nov. 26; 128 (22):2372-83. doi: 10.1161/CIRCULATIONAHA.113.002481, electronically published Sep. 6, 2013) was presented at HRS 2014 and demonstrated that in a retrospective analysis of approximately 40,000 Boston Scientific ICD patients connected with remote management there was both improved survival and lower rates of hospitalization over a three-year time frame.

Current guidelines recommend using remote management for implantable devices, but the patterns of adoption of this technology depend on the enrollment of the patient into a remote management system and subsequent activation of remote management by the physician and an effective remote management program. Remote management is used in far less than half of eligible patients and data has demonstrated that lack of enrollment is the major cause of underutilization, and this primarily relates to the local practice environment (Akar et al., "Use of remote monitoring of newly implanted cardioverter-defibrillators: insights from the patient related determinants of ICD remote monitoring (PREDICT RM) study," Circulation 128, pp. 2372-2373, Nov. 25, 2013). The advantages of remote management would be most realized when treating patients at risk for CHF.

According to the American Heart Association Heart Disease and Stroke Statistics 2014 Update, approximately 5.1 million persons in the United States have clinical manifestations of CHF, with continued increasing prevalence (Go et al.; on behalf of the American Heart Association Statistics Committee and Stroke Statistics Subcommittee, "Heart disease and stroke statistics-2014 update: a report from the American Heart Association," Circulation 2014; 129:e28-292.). Approximately 650,000 new cases of CHF are diagnosed annually (Yancy et al. 2013, "ACCF/AHA guideline for the management of heart failure: a report of the American College of Cardiology Foundation/American Heart Association Task Force on Practice Guidelines," J Am Coll Cardiol 2013; 62:e147-239). Depending on the study, the prevalence of asymptomatic LV dysfunction ranges from 6% to 21%. It is projected that by the year 2030, the economic burden of HF will increase approximately 127% to $69.7 billion in the United States compared to 2012 (Heidenreich et al., "Forecasting the impact of heart failure in the United States: a policy statement from the American Heart Association," Circ Heart Fail 2013; 6:606-19). Multiple epidemiological studies have demonstrated that the prevalence of CHF with a normal ejection fraction is in the range of 50-55%, and is seen largely in the elderly population (Owan et al., "Trends in prevalence and outcome of heart failure with preserved ejection fraction," N Engl J Med 2006; 355:251-9). Readmissions for HF remains disturbingly common, with significant quality of life and economic repercussions. Data has demonstrated that among 1,077 patients with HF, 83% of patients were hospitalized at least once after the diagnosis of HF and 43% were hospitalized at least four times (Dunlay et al., "Hospitalizations after heart failure diagnosis: a community perspective," J Am Coll Cardiol 2009; 54:1695-702). Multiple hospitalizations, particularly of elderly patients with multiple comorbid conditions (50% have three or more), are especially common. It has been found that the 3-month readmission rate after an index hospitalization for HF was as high as 47% of discharges, leading to the fact that more Medicare dollars are spent on HF than on any other diagnosis (Rich et al., "A multidisciplinary intervention to prevent the readmission of elderly patients with congestive heart failure," N Engl J Med 1995; 333:1190-5).

Currently implanted ICDs, ICD-CRTs, and implanted cardiac devices have technologies that monitor patients for CHF. By way of example, a CIED known as the CardioMEMS monitor (St. Jude Medical, CRMD, St. Paul, Minn.) measures pressure in the pulmonary artery ("PA") and provides the clinician with means to monitor PA pressure daily via wireless data communication and help direct management of CHF via RM. The CardioMEMS monitor was analyzed in a recent randomized trial of 550 patients with NYHA class III CHF (CHAMPION trial—Abraham et al., "Wireless pulmonary artery haemodynamic monitoring in chronic heart failure: a randomised controlled trial," Lancet 2011; 377:658-66). Daily measurement of pulmonary artery pressures utilizing the CardioMEMs device with wireless transmission of data to a centralized electronic surveillance system was associated with a 36% reduction in HF admissions during a mean follow-up period of 15 months (p<0.001).

Additionally, CHF thoracic impedance monitors are present on the far majority of ICDs implanted today. These monitors record electrical impedance across the thorax as measured between electrodes present on the device's intracardiac leads and ICD device can. Decreases in impedance identify pulmonary vascular congestion (e.g., fluid buildup in the lungs) and can trigger alerts to patients (e.g., a vibratory or audible signal) and the following physicians via the RM network. Published data has demonstrated that CRM device impedance based CHF monitors can detect pulmonary vascular congestion before adverse clinical outcome. This may occur due to a weak heart, for example, in patients with cardiomyopathy and systolic congestive heart failure, or because of a heart that does not have normal relaxation properties (e.g., diastolic heart failure). The recent Implant-based Multiparameter Telemonitoring of Patients with Heart Failure trial demonstrated that daily automatic RM enabled early action to be taken in response to the warning signs of decompensated heart failure and a lower all-cause mortality and hospital admission rate for CHF (Hendricks et al., "Implant-based Multiparameter Telemonitoring of Patients with Heart Failure (IN-TIME); a randomized controlled trial," The Lancet 2014; 384: 583-590). Thus, data supports the conclusion that RM compliance improves outcome for patients at risk for CHF and in turn will benefit the health care system at large.

EMRs and electronic prescription systems perform a means to crosscheck medications and patient diagnoses to screen for contraindications and flag clinicians. No currently available methods are available to evaluate whether or not health care providers properly remotely monitor patients with implanted cardiac devices, or multi-level assessment of patient, physician, health care system/provider compliance with standard of care diagnostic testing and therapeutic measures.

Given the above background, what is needed in the art are systems and methods for determining health care provider monitoring compliance.

SUMMARY

The present disclosure discloses systems and methods for determining health care provider monitoring compliance. Embodiments of the present disclosure include methods and algorithms for monitoring a health care delivery system's compliance with delivery of standard of care treatment and performing diagnostic tests in at risk patient subgroups including but not limited to monitoring of patients with implanted cardiac devices. The methodologies include assessment of compliance of patients, physicians, hospitals, and health care delivery systems, and notification of shortcomings in standard of care. In one embodiment, a compliance algorithm provides an overseeing organization, such as a governmental body, a hospital administration, or a health insurance company, with a means to monitor the proper delivery of standard of care for patients implanted with cardiac devices capable of wireless transmission of alert conditions. Acquired data is utilized to derive an index of compliance that is evaluated to ensure meaningful use dispensing medications, ordering appropriate tests, and delivering optimal patient care. Context management is implemented to facilitate data transmission, interface disparate applications, and provide feedback to the relevant parties in real time through simple portals/graphical user interfaces where data is input and compliance measures reviewed at appropriate time intervals. for determining health care provider monitoring compliance One aspect of the present disclosure provides a computer system for determining health care provider monitoring compliance. The computer system comprises one or more processors and a memory. The memory comprises non-transitory instructions which, when executed by the one or more processors, perform a method. The method comprises performing a first autonomous process, a second autonomous process, and a third (autonomous or non-autonomous) process.

In the first autonomous (automatic, without human intervention) process, for each respective data element in a plurality of data elements, the respective data element in the plurality of data elements is obtained from a corresponding medical device in a corresponding subject in a first plurality of subjects. In some embodiments the corresponding medical device is implanted in the corresponding subject. In some embodiments the corresponding medical device is connected to the corresponding subject. In some embodiments the corresponding medical device is worn by the corresponding subject. In some embodiments the corresponding medical device is associated with but not worn by or implanted in the corresponding subject. The respective data element is interrogated to determine a condition of the medical device or to determine a condition of the corresponding subject. Responsive to the interrogating, (i) a first medical code that indicates that the condition of the medical device or the condition of the corresponding subject has been evaluated and (ii) an associated timestamp for the act of interrogating the medical device are recorded in a medical record associated with the corresponding subject.

The second autonomous process is performed on a recurring basis (e.g., at each respective epoch in a plurality of epochs. The second autonomous process comprises, for each respective subject in a second plurality of subjects, determining whether the first medical code has been recorded in the medical record associated with the respective subject during the respective epoch by parsing the medical record for the first medical code and, when found in the medical record, using the associated timestamp to determine if the first medical code is associated with the respective epoch. The second autonomous process advances a compliance counter when the medical record associated with the respective subject includes the first medical code associated with the respective epoch. The second autonomous process advances a noncompliance counter when the medical record associated with the respective subject does not include the first medical code associated with the respective epoch. The first plurality of subjects constitutes all or a portion of the second plurality of subjects. That is, typically, the first plurality of subjects is a subset of the second plurality of subjects. In some embodiments, each subject in the second plurality of subjects has an implanted medical device. In some embodiments, each subject in the second plurality of subjects has a wearable medical device. In some embodiments, each subject in the second plurality of subjects is associated with a medical device.

The third process comprises any combination of the following: (i) receiving a compliance request and, responsive to the compliance request, providing compliance information in accordance with the compliance counter or the noncompliance counter, (ii) providing one or more suggested treatment options based upon the compliance information, and/or (iii) providing a list of subjects, where the list of subjects is identified from the second plurality of subjects on the basis that they (a) share one or more characteristics and (b) the medical records of the list of subjects indicate they lack a specific therapy or a treatment that is deemed the standard of care for subjects having the one or more characteristics.

In some embodiments, the corresponding medical device is a cardiac implantable electronic device. In some such embodiments, the cardiac implantable electronic device is a permanent pacemaker, an implantable cardioverter defibrillator, a cardiac resynchronization therapy device, a monitor of congestive heart failure, or an implantable loop recorder.

In some embodiments, the interrogating the data element in the first autonomous process determines the condition of the corresponding subject selected from the group consisting of a pulmonary artery pressure, an intra-thoracic impedance, an atrial arrhythmia, a ventricular arrhythmia, measurement of cardiorespiratory structure/function, an index of congestive heart failure, and a pulmonary vascular congestion.

In some embodiments, the interrogating the data element in the first autonomous process determines the condition of the corresponding subject, where the condition is an index of cardiorespiratory function. In some such embodiments, the condition is hyperlipidemia, a thoracic impedance index of pulmonary vascular congestion, a mean heart rate, or a cardiac inotropic state.

In some embodiments, the first medical code is an ICD-9 code, an ICD-10 code, a Current Procedure Terminology (CPT) code, or an equivalent thereof.

In some embodiments, the first medical code is extracted from the context of the medical record thereby providing semantic interoperability without specific reliance on a coding standard. That is, the medical code is not per se included in the medical record but nevertheless a determination is made that the work associated with the medical code was performed based on the context of the medical record.

In some embodiments, the interrogating the data element in the first autonomous process determines the condition of the corresponding subject, where the condition is an index of cardiorespiratory function, and each respective epoch in the plurality of epochs is a day.

In some embodiments, each respective epoch in the plurality of epochs is the same length of time. For example, in some embodiments, each respective epoch in the plurality of epochs is an hour or less, a day or less, two days or less, a week or less, a month or less, or a quarter of a year or less.

In some embodiments, the corresponding medical device is implanted in the corresponding subject and wirelessly transmits the respective data element. In some embodiments, the corresponding medical device is connected to the corresponding subject and wirelessly transmits the respective data element.

In some embodiments, the interrogating of the data element in the first autonomous process determines the condition of the corresponding subject and the first autonomous process further comprises generating an alert for the corresponding subject when determination of the condition in the corresponding subject triggers an alert rule, and a nature of the alert (e.g., contacting a health care practitioner, a buzzer alarm, a warning signal, triggering an E-mail or SMS message to a health care practitioner, etc.) specified by the alert rule. In some such embodiments, the condition is one or more index of cardiorespiratory function.

In some embodiments, the medical record is an electronic medical record.

In some embodiments, the first autonomous process and the second autonomous process occur concurrently. In some embodiments, the first autonomous process, the second autonomous process, and the third process occur concurrently.

In some embodiments, the second plurality of subjects is associated with a physician, a provider group, a hospital, a hospital network, a health insurance company, a pharmacy, a governmental body, or a prescribing clinician.

In some embodiments, the second plurality of subjects is associated with a physician, a provider group, a hospital, a hospital network, a health insurance company, a pharmacy, a governmental body or a prescribing clinician, each subject in the plurality of subjects has a pathologic condition, the interrogating the data element in the first autonomous process determines a condition of the medical device, and the corresponding medical device of the corresponding subject wirelessly transmits the respective data element. In some such embodiments, the pathologic condition is cardiomyopathy, congestive heart failure, arrhythmia, a cardiorespiratory impairment, or a neurologic ailment.

In some embodiments, the second plurality of subjects is associated with a physician, a provider group, a hospital, a hospital network, a health insurance company, a pharmacy, a governmental body, or a prescribing clinician, each subject in the plurality of subjects has cardiomyopathy or congestive heart failure, the interrogating the data element in the first autonomous process determines the condition of the corresponding subject, where the condition is a pathologic condition, and the corresponding medical device of the corresponding subject wirelessly transmits the respective data element. In some such embodiments, the pathologic condition is cardiomyopathy, congestive heart failure, arrhythmia, a cardiorespiratory impairment, or a neurologic ailment.

In some embodiments, a length of each respective epoch in the plurality of epochs is set by an epoch period and the second autonomous process further comprises, at the end of an epoch in the plurality of epochs, determining a compliance for the second plurality of subjects using the compliance counter or the noncompliance counter, where, when the compliance for the second plurality of subject fails to satisfy a compliance threshold, the length of the epoch period is shortened.

In some embodiments, the second plurality of subjects is associated with a physician, a provider group, a hospital, a hospital network, a health insurance company, a pharmacy, a governmental body, or a prescribing clinician, each subject in the second plurality of subjects has been diagnosed with an ailment, and each subject in the second plurality of subjects has been coded for hospital readmission for the ailment.

In some embodiments, the second plurality of subjects is associated with a physician, a provider group, a hospital, a hospital network, a health insurance company, a pharmacy, a governmental body, or a prescribing clinician, and each subject in the second plurality of subjects satisfies a set of screening criteria. In some such embodiments, the set of screening criteria comprises (i) historical tobacco use, (ii) male, and (iii) over 65 years of age, and the interrogating the data element in the first autonomous process determines a condition of the corresponding subject, where the condition is whether a predetermined treatment regimen has been performed on the corresponding subject. In some such embodiments, the set of screening criteria comprises two or more criteria, and the interrogating the data element in the first autonomous process determines a condition of the corresponding subject, where the condition is whether a predetermined treatment regimen has been performed on the corresponding subject. In some such embodiments, the set of screening criteria comprises four or more criteria, and the interrogating the data element in the first autonomous process determines a condition of the corresponding subject, where the condition is whether a predetermined treatment regimen has been performed on the corresponding subject. In some such embodiments, the set of screening criteria comprises ten or more criteria, and the interrogating the data element in the first autonomous process determines a condition of the corresponding subject, wherein the condition is whether a predetermined treatment regimen has been performed on the corresponding subject.

In some embodiments, the first medical code is a Current Procedure Terminology (CPT) code selected from the group consisting of 93294, 93295, 93296, 93297, 93298, 93299, 93279, 93280, 93281, 93282, 93283, 93284, 93285, 93288, 93289, and 93290, or an equivalent thereof.

In some embodiments, the first medical code is representative of one or more of an in office interrogation, reprogramming, fitting or adjustment of the corresponding medical device or a remote monitoring evaluation of the corresponding medical device.

In some embodiments, the first medical code is an ICD-10 code selected from the group consisting of Z95.0, Z45.018, Z95.810, and Z45.02, or an equivalent thereof.

In some embodiments, the interrogating the data element in the first autonomous process determines the condition of the corresponding subject. In some such embodiments, the condition of the corresponding subject is selected from the group consisting of cardiomyopathy, congestive heart failure, arrhythmia, cardiorespiratory impairment, or a neurologic ailment.

In some embodiments, the first medical code is an ICD-10 code selected from the group consisting of I63.4, I63.40, I63.41, I63.411, I63.412, I63.413, I63.419, I63.42, I63.421, I63.422, I63.423, I63.429, I63.43, I63.431, I63.432, I63.433, I63.439, I63.44, I63.441, I63.442, I63.443, I63.449, I63.49, I63.1, I63.10, I63.11, I63.111, I63.112, I63.113, I63.119, I63.12, I63.13, I63.131, I63.132, I63.133, I63.139, I63.19, or I63.9, or an equivalent thereof.

In some embodiments, the interrogating the data element in the first autonomous process determines the condition of the corresponding subject, where the condition is selected from the group consisting of an illness resulting in hospital readmissions, an identifying factor for risk of congestive heart failure, an abnormality in heart rate, an abnormality in heart rhythm, a need for frequent right ventricular pacing, an alteration in electrical conduction, an alteration in electromechanical synchrony, an index of congestive heart failure, a pulmonary vascular congestion, a risk for thromboembolism or stroke, a risk for arrhythmia, syncope, a risk for syncope, a risk for progressive congestive heart failure, a risk for implanted device or device lead malfunction, a risk for myocardial infarction, a risk for a vascular complication, a risk for a pulmonary complication, a risk for a complication due to diabetes, a risk for complication due to hypertension, a risk for renal failure, an index of cardiac inotropic state, or a genotype profile that identifies risk for specific predetermined disease state.

In some embodiments, the first autonomous process further comprises recording, responsive to the interrogating, (a) a plurality of medical codes in the medical record associated with the corresponding subject that collectively indicate the condition of the medical device and/or the condition of the corresponding subject, where the plurality of medical codes includes the first medical code. In such embodiments, the compliance information reported by the third process is based upon the prevalence of the plurality of medical codes in the medical records of the second plurality of subjects across a subset or across all the epochs in the plurality of epochs. In some such embodiments, the plurality of medical codes comprises two different medical codes, three different medical codes, four different medical codes, or five or more different medical codes.

In some embodiments, the second autonomous process further comprises determining whether each subject in the plurality of subjects has been prescribed a medication by parsing the medical record associated with each subject in the second plurality of subjects for an indication of the medication. In some such embodiments, the medication is for a beta blocker, a lipid lowering therapy, an angiotensin converting enzyme inhibitor, an angiotensin receptor blocker, an aldosterone receptor blocker, hydralazine, a nitrate, a PCSK9 inhibitor, a negative chronotropic agent, a hyperpolarization-activated cyclic nucleotide-gated channel blocker, an anti-platelet agent, an anti-coagulant, a Neprilysin inhibitor, or a cardiac sinus node inhibitor. In some such embodiments, the presence of the indication of the medication in the medical records corresponding to the second plurality of subjects contributes to the compliance information.

In some embodiments, the second autonomous process further comprises determining whether each subject in the second plurality of subjects has been prescribed a supplemental medical device by parsing the medical record associated with each subject in the second plurality of subjects for a second medical code. In such embodiments, the supplemental medical device is a cardiac rhythm management device, a cardiac rhythm management device configured to monitor or treat congestive heart failure, a heart failure treatment device, a respiratory support apparatus, a non-invasive ventilation therapy, or a continuous positive airway pressure device. In some such embodiments, the presence of the second medical code in the medical records corresponding to the second plurality of subjects contributes to the compliance information.

In some embodiments, the second autonomous process further comprises determining whether each subject in the second plurality of subjects has been prescribed a supplemental therapy by parsing the medical record associated with each subject in the second plurality of subjects for a second medical code. In such embodiments, the supplemental therapy is non-invasive ventilation therapy. In some such embodiments, the presence of the second medical code in the medical records corresponding to the second plurality of subjects contributes to the compliance information.

In some embodiments, each corresponding medical device is a pacemaker and the second autonomous process further comprises identifying the second plurality of subjects by scanning the medical record associated with each subject in a third plurality of subjects for a second code. In such embodiments, the second plurality of subjects is all or a portion of the third plurality of subjects. The second code is ICD-10 Z95.0, ICD-10 Z45.018, CPT 93279, CPT 93280, or CPT 93281, and the first code is CPT 93294 or CPT 93296.

In some embodiments, each corresponding medical device is a defibrillator and the second autonomous process further comprises identifying the second plurality of subjects by scanning the medical record associated with each subject in a third plurality of subjects for a second code. In such embodiments, the second plurality of subjects is all or a portion of the third plurality of subjects. That is, the second plurality of subjects is typically a subset of the third plurality of subjects. In some such embodiments, the second code is ICD-10 Z95.810, Z45.02, CPT 93282, CPT 93283, or 93284, or an equivalent thereof, and the first code is CPT 93295 or 93296, or an equivalent thereof.

In some embodiments, the second autonomous process further comprises identifying the second plurality of subjects by scanning the medical record associated with each subject in a third plurality of subjects for a second code. The second plurality of subjects is all or a portion of the third plurality of subjects. That is, the second plurality of subjects is typically a subset of the third plurality of subjects. In such embodiments, the second code is ICD-10 I44.7, ICD-10 Z95.810, CPT 93282, or CPT 93283, or an equivalent thereof, and the first code is CPT 93284 or an equivalent thereof.

In some embodiments, the second autonomous process further comprises identifying the second plurality of subjects by scanning the medical record associated with each subject in a third plurality of subjects for a second code. The second plurality of subjects is all or a portion of the third plurality of subjects. That is, the second plurality of subjects is typically a subset of the third plurality of subjects. In such embodiments, the second code is a combination of a first CPT code or ICD-10 code, or equivalent thereof, identifying that a subject has an implanted cardiac rhythm management device that does not include cardiac resynchronization therapy and a second CPT or second ICD-10 code, or equivalent thereof, identifying the patient as having congestive heart failure or risk for congestive heart failure. In some such embodiments, the first CPT code or ICD-10 code is ICD-10 Z95.0, ICD-10 Z45.018, ICD-10 Z45.02 or ICD-10 Z95.810, and the second CPT code or ICD-10 code is ICD-10 I44.7, ICD-10 I44.2, ICD-10 I44.3, ICD-10 I50.22, ICD-10 I50.23, ICD-10 I50.32, ICD-10 I50.42, ICD-10 I50.43, or ICD-10 I50.20.

In some embodiments, the second autonomous process further comprises identifying the second plurality of subjects by scanning the medical record associated with each subject in a third plurality of subjects for a second code, the second plurality of subjects is all or a portion of the third plurality of subjects, and the second code is a CPT code identifying the patient as having cardiac resynchronization therapy. In some such embodiments the CPT code is 93281 or 93284.

In some embodiments, the second autonomous process further comprises identifying the second plurality of subjects by scanning the medical record associated with each subject in a third plurality of subjects for a second code. The second plurality of subjects is all or a portion of the third plurality of subjects. That is, the second plurality of subjects is typically a subset of the third plurality of subjects. In such embodiments, the second code is an ICD-10 code, or equivalent thereof, identifying the patient as having cardiac resynchronization therapy. In some such embodiments, the ICD-10 code is in the I44.x or I50.yy families of ICD-10 codes, or is an equivalent thereof.

In some embodiments, each corresponding medical device is an implantable loop recorder. In some such embodiments, the second autonomous process further comprises identifying the second plurality of subjects by scanning the medical record associated with each subject in a third plurality of subjects for a second code. The second plurality of subjects is all or a portion of the third plurality of subjects. The second code is a second CPT-10 code, or equivalent thereof, that identifies a corresponding subject as having an implantable loop recorder evaluated in the office, and the first code is a first CPT-10 code, or equivalent thereof, that identifies whether or not the corresponding subject's implantable loop recorder is being monitored remotely at designated (specific) time intervals.

In some embodiments, the first code is CPT-10 93298 or 93299 (or an equivalent thereof), and the second code is CPT-10 92385 (or an equivalent thereof).

In some embodiments, each corresponding medical device is an implantable loop recorder and the second autonomous process further comprises identifying the second plurality of subjects by scanning the medical record associated with each subject in a third plurality of subjects for a second code. The second plurality of subjects is all or a portion of the third plurality of subjects. That is, the second plurality of subjects is typically a subset of the third plurality of subjects. The second code is an ICD-10 code, within the family of ICD-10I63.4, ICD-10I63.1, or 163.9, or equivalent thereof. The first code is CPT 93285 or CPT 93298.

In some embodiments, the third process identifies the absence of an expected treatment or diagnostic modality or provides a suggested treatment for a subject in the first plurality of subjects when the compliance information indicates that treatment for the subject has failed a compliance threshold over the plurality of epochs.

In some embodiments, the third process identifies the absence of an expected treatment or diagnostic modality, or provides a suggested treatment for a subset of subjects in the first plurality of subjects when the compliance information indicates that treatment for the subset of subjects has failed a compliance threshold over the plurality of epochs.

In some embodiments, the respective data element in the plurality of data elements from the corresponding medical device provides a condition of the subject that is recorded in the medical record associated with the subject and wherein the third process provides a suggested treatment for the subject based upon the condition or identifies the absence of an expected treatment or diagnostic modality. In some embodiments, the condition is an irregular heartbeat and the suggested treatment regimen is a medication for the irregular heartbeat. In some embodiments, the condition is a thoracic impedance measurement that indicates that the subject has congestive heart failure and the one or more suggested treatment options is to provide the subject with a device that provides resynchronization therapy or biventricular pacing when the subject's record indicate that they have not been provided with resynchronization therapy or biventricular pacing.

In some embodiments, the compliance counter and the noncompliance counter are two separate counters. In some embodiments, the compliance counter and the noncompliance counter are a single counter.

Another aspect of the present disclosure provides a method for determining health care provider monitoring compliance. The method comprises performing a first autonomous process, a second autonomous process, and a third process. For each respective data element in a plurality of data elements, the first autonomous process comprises obtaining the respective data element in the plurality of data elements from a corresponding medical device of a corresponding subject in a first plurality of subjects. In some embodiments, the corresponding medical device is connected to the corresponding subject. In some embodiments, the corresponding medical device is implanted in the corresponding subject. In some embodiments, the corresponding medical device is worn by the corresponding subject. In some embodiments, the corresponding medical device is associated with but not worn by the corresponding subject. The respective data element is interrogated to determine a condition of the medical device or to determine a condition of the corresponding subject. The first autonomous process records, responsive to the interrogating, a first medical code that indicates that the condition of the medical device or the condition of the corresponding subject has been evaluated and an associated timestamp for the interrogating in a medical record associated with the corresponding subject. The method also performs a second autonomous process at each respective epoch in a plurality of epochs. The second autonomous process comprises, for each respective subject in a second plurality of subjects, determining whether the first medical code has been recorded in the medical record associated with the respective subject during the respective epoch. This is done by parsing the medical record for the first medical code and, when found in the medical record, using the associated timestamp to determine if the first medical code is associated with respective epoch. A compliance counter is advanced when the medical record associated with the respective subject includes the first medical code associated with the respective epoch. A noncompliance counter is advanced when the medical record associated with the respective subject does not include the first medical code associated with the respective epoch. The first plurality of subjects constitutes all or a portion of the second plurality of subjects and each subject in the second plurality of subjects has an implanted medical device. The method also performs a third process. The third process comprises (i) receiving a compliance request and, responsive to the compliance request, providing compliance information in accordance with the compliance counter or the noncompliance counter, (ii) providing one or more suggested treatment options based upon the compliance information, and/or (iii) providing a list of subjects, where the list of subjects is identified from the third plurality of subjects on the basis that they (a) share one or more characteristics and (b) the medical records of the subjects indicate they lack a specific therapy or a treatment that is standard of care for subjects having the one or more characteristics.

Another aspect of the present disclosure provides a non-transitory computer readable storage medium, where the non-transitory computer readable storage medium stores instructions, which when executed by a computer system, cause the computer system to perform any of the methods for determining health care provider monitoring compliance described in the present disclosure.

BRIEF DESCRIPTION OF THE DRAWINGS

FIGS. 4A, 4B, 4C, 4D, 4E, 4F, 4G, 4H, 4I, and 4J collectively provide a flow chart of processes and features of a computer system for determining health care provider monitoring compliance in accordance with various embodiments of the present disclosure.

In FIG. 5, element 500 is the subject, CIED is the implanted device, 200 is the data collection device (e.g., home monitoring system), 250 is the health care system (e.g., CRM company's central hub for acquiring data from 200), and 40 is the terminal for downloading remote monitoring data at the level of the provider to a querying party 50. EMR is an electronic medical record system which inputs data into the compliance calculator. The terms x, y, and z depict wireless connectivity and means for data transfer between a patient's CIED, the home monitoring system at 200, the health care system 250 (e.g. the CRM company's hub), and the provider's terminal for downloading RM data at 40, respectively. Feedback on compliance, a, is provided to the provider.

Like reference numerals refer to corresponding parts throughout the several views of the drawings.

DETAILED DESCRIPTION

The present disclosure generally relates to systems and methods for remotely monitoring a health care provider's and health care network's compliance delivering standard of care treatment for patients and gauging interim improvements in compliance at regular intervals based on measured indices of compliance. The present disclosure teaches a method for confirming that patients' health care providers are properly monitoring their medical devices (e.g., implanted cardiovascular devices) via remote connectivity and deriving an index of compliance based on input diagnostic and treatment codes input to an electronic medical record and providing feedback to all parties on level of compliance, and confirming proper billing, coding and reimbursement for services provided.

The methods and algorithms described herein are designed for implementation by a health care system to help identify patients who are not receiving indicated therapy by their health care providers and oversee clinicians providing such care. The embodiments presented are exemplary and, for purposes of explanation, relate to the identification of patients with devices (e.g., implanted cardiac devices) who are not adequately followed by remote monitoring ("RM") systems and evaluating provider compliance with enrolling patients into a RM system. The described systems and methods described can be used in any number of clinical scenarios including identification of patients implanted with cardiac devices that have not successfully enrolled into a remote management system or patients suffering from congestive heart failure who would stand to benefit from having clinical indices (e.g., pulmonary artery pressure, intra-thoracic impedance) remotely monitored by implanted cardiac devices. Remote management of devices (e.g., cardiac devices) improves quality of life, reduces hospitalizations and readmissions, and optimizes cost effective health care on a global level.

For system operation, data extracted from inpatient ICD-9 or ICD-10, CPT codes, hospital codes, modifiers, etc., e-prescribing systems, and the like are input and analyzed to identify those providers who are not delivering standard of care treatment and those patients at risk for complications, adverse outcome, re-hospitalizations due to their own non-compliance. The check and balance system functions to evaluate compliance of patients, individual physicians, ancillary clinicians, physician practices, health care insurance companies, hospitals, pharmacies, and hospital networks and also maintains a fiscally sound mechanism to support effective delivery of health care and oversight.

Figure 1:
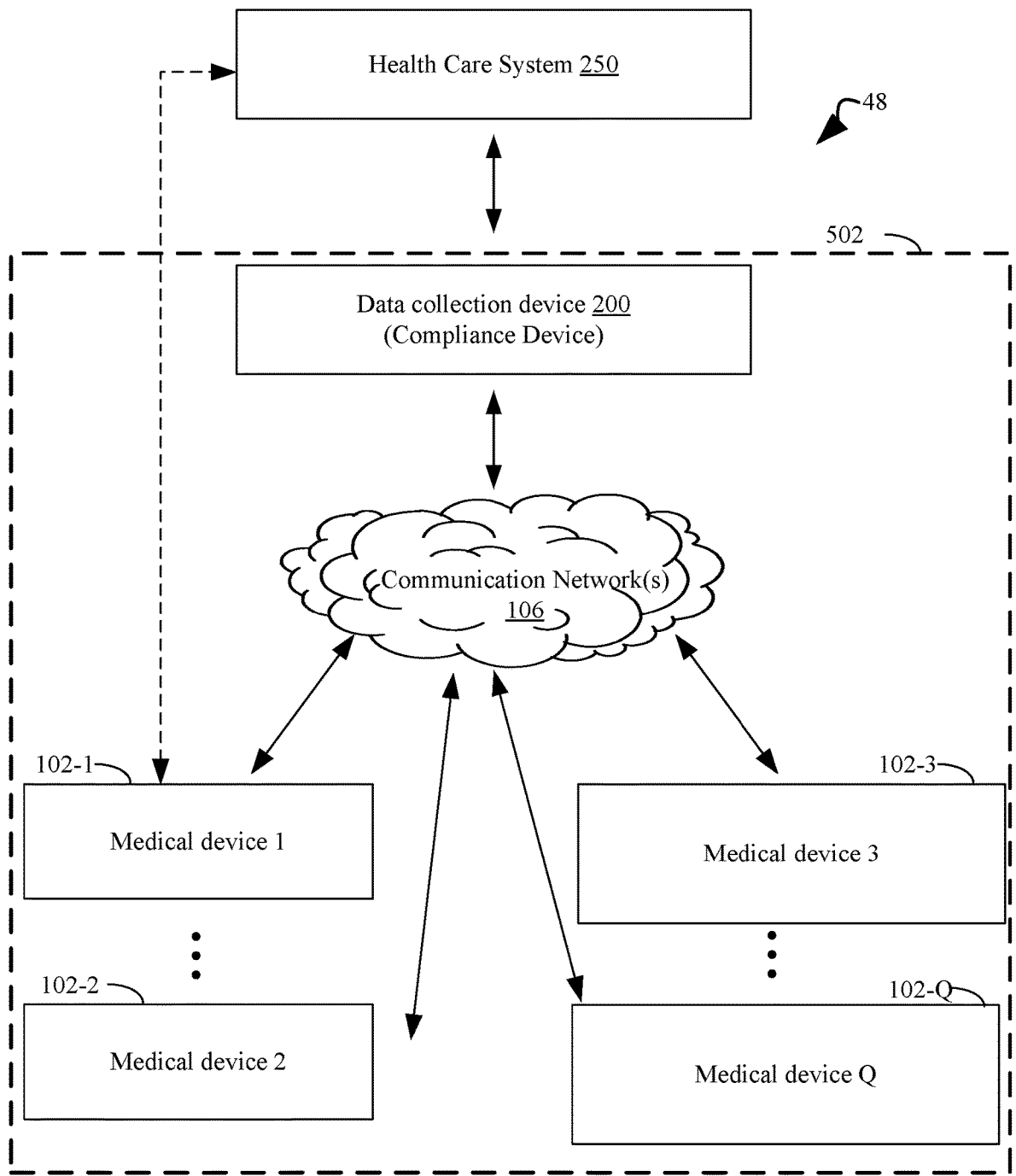
FIG. 1 illustrates an exemplary system topology that includes a health care system for determining health care provider monitoring compliance, a data collection device for collecting patient data from medical devices, and medical devices associated with subjects, where the above-identified components are interconnected, optionally through a communications network, in accordance with an embodiment of the present disclosure.

The present disclosure relies upon the acquisition of a plurality of data elements, where each data element in the plurality of data elements is from a corresponding medical device of a corresponding subject in a first plurality of subjects. In some embodiments, the corresponding medical device is implanted in the corresponding subject. FIG. 1 illustrates an example of an integrated system 48 for the acquisition of such data. The integrated system 48 includes one or more medical devices 102, each associated with a different subject, a data collection device 200, and a health care system 250.

With the integrated system 48, data elements from the medical devices 102 of subjects are obtained. Each data element comprises a condition of the medical device or a condition of the corresponding subject measured by the medical device. The plurality of data elements are used to determine health care provider monitoring compliance in accordance with the methods of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
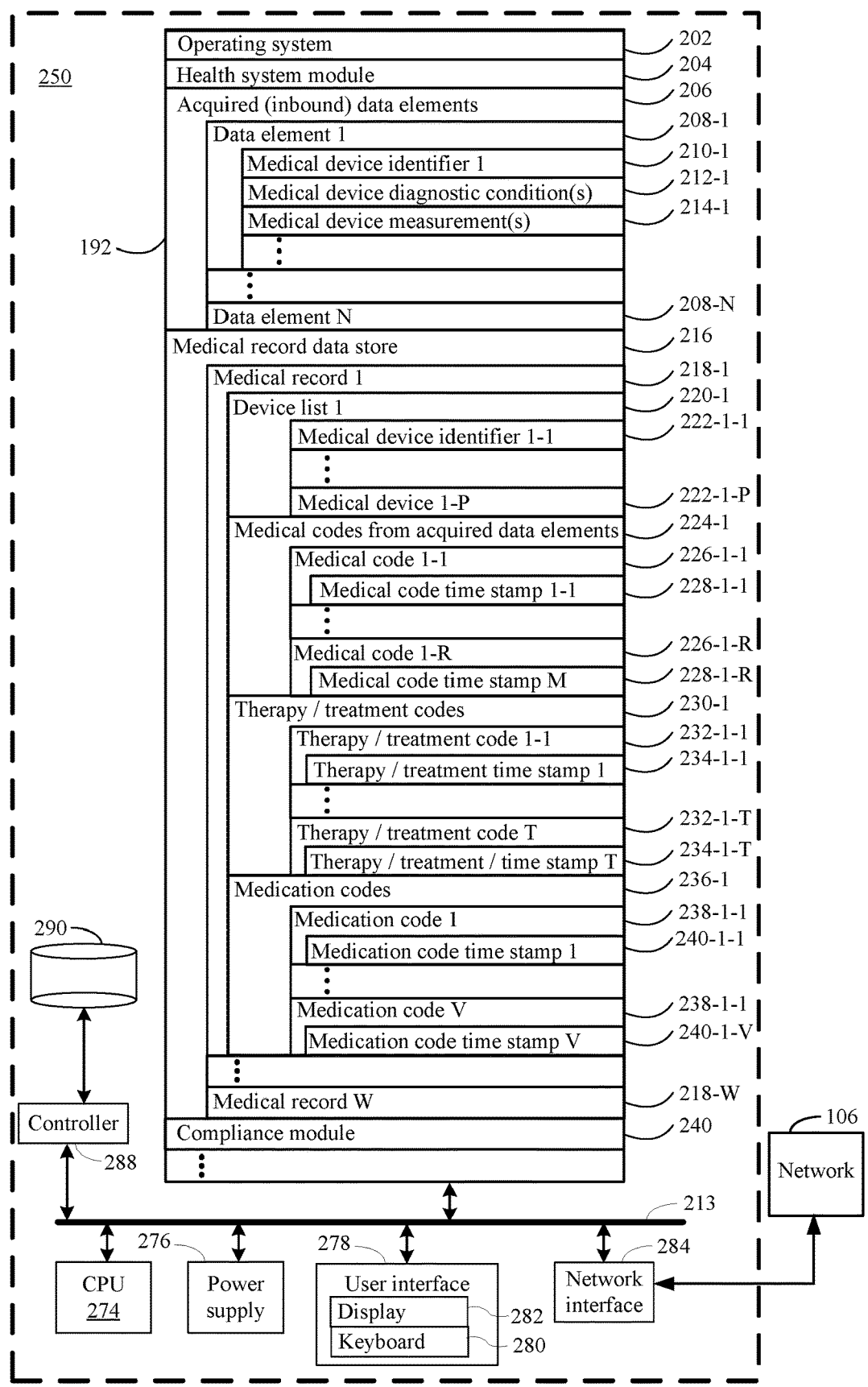
FIG. 2 illustrates a health care system for determining health care provider monitoring compliance in accordance with an embodiment of the present disclosure.
Figure 3:
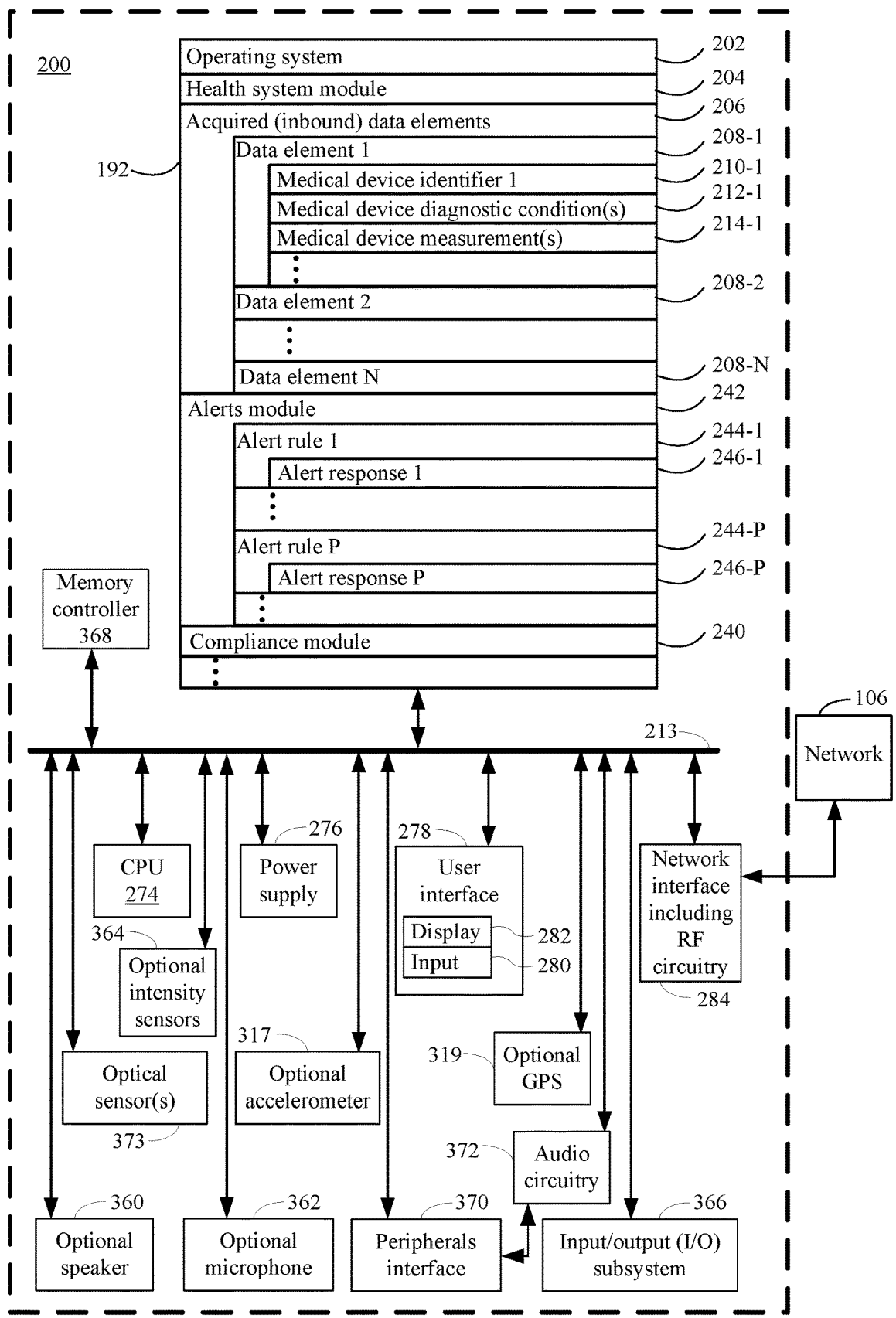
FIG. 3 illustrates a data collection device (e.g., the home monitoring system) for collecting patient data from medical devices in accordance with an embodiment of the present disclosure.

A detailed description of a system 48 for determining health care provider monitoring compliance in accordance with the present disclosure is described in conjunction with FIGS. 1 through 3. As such, FIGS. 1 through 3 collectively illustrate the topology of the system in accordance with the present disclosure. In the topology, there is a health care system 250 for receiving a plurality of data elements from a plurality of subjects and using these data elements to ascertain health care provider monitoring compliance ("health care system 250") (FIGS. 1, and 2), a data collection device 200 (e.g., a home monitoring system) (FIGS. 1 and 3), and one or more medical devices 102 associated with each subject (FIG. 1). Throughout the present disclosure, the data collection device 200 and the health care system 250 will be referenced as separate devices solely for purposes of clarity. That is, the disclosed functionality of the data collection device 200 and the disclosed functionality of the health care system 250 are contained in separate devices as illustrated in FIG. 1. However, it will be appreciated that, in fact, in some embodiments, the disclosed functionality of the data collection device 200 and the disclosed functionality of the health care system 250 are contained in a single device.

Although not depicted in FIG. 1, typical embodiments where the data collection device 200 is not subsumed by the health care system 250, there is a different data collection device 200 associated with each subject. As such, in typical embodiments, there is a many-to-one relationship between the data collection device 200 and the health care system 250. Moreover, in typical embodiments, there is a single medical device 102 for each subject and thus there is typically a one-to-one relationship between each medical device 102 and a corresponding data collection device 200.

Referring to FIG. 1, the health care system 250 determines health care provider monitoring compliance. To do this, each data collection device 200, which is in electrical communication with the health care system 250, receives data elements originating from a one or medical devices 102 that have been provided to a corresponding patient (subject) of the health care provider. Each such data element comprises a condition of the medical device 102 or a condition of the corresponding subject that was made by the medical device 102. In some embodiments, the data collection device 200 receives the data elements directly from the medical device 102. For instance, in some embodiments the data collection device 200 receives the data element wirelessly through radio-frequency signals. In some embodiments, such signals are in accordance with an 802.11 (WiFi), Bluetooth, or ZigBee standard. In some embodiments, the data collection device 200 receives the data elements directly, analyzes the data, and passes the analyzed data to the health care system 250. In some embodiments, a medical device 102 includes an RFID tag and communicates the data element to the data collection device 200 and/or the health care system 250 using RFID communication.

In some embodiments, the data collection device 200 and/or the health care system 250 is not proximate to the subject and/or does not have wireless capabilities or such wireless capabilities are not used for the purpose of acquiring data elements. In such embodiments, a communication network 106 may be used to communicate data elements from the medical device 102 to the data collection device 200 and/or the regimen timing device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 other than the one depicted in FIG. 1 are possible. For instance, rather than relying on a communications network 106, the one or more medical devices 102 may wirelessly transmit information directly to the data collection device 200 and/or health care system 250. Further, the data collection device 200 and/or the health care system 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the health care system 250 comprises one or more computers. For purposes of illustration in FIG. 2, the health care system 250 is represented as a single computer that includes all of the functionality for determining health care provider monitoring compliance. However, the disclosure is not so limited. In some embodiments, the functionality for determining health care provider monitoring compliance is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary health care system 250 for determining health care provider monitoring compliance comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the health care system 250 but that can be electronically accessed by the health care system 250 over an Internet, intranet, or other form of network or electronic cable (illustrated as element 106 in FIG. 2) using network interface 284.

In some embodiments, the memory 192 of the health care system 250 for determining health care provider monitoring compliance stores:

an operating system 202 that includes procedures for handling various basic system services;

a health system module 204 for tracking health care provider monitoring compliance;

a plurality of acquired (inbound) data elements from data collection devices or medical devices 102, each such data element 208 optionally including a medical device identifier 210 that identifies the originating medical device 102, one or more medical device diagnostic conditions 212, and one or more medical device measurements 214;

a medical record data store 216 that stores a plurality of medical records, where each respective medical record 218 in the plurality of medicals is for a corresponding health care provider subject and optionally stores a device list 220 that includes the medical device identifier 222 of each medical device 102 associated with (e.g. implanted in) the corresponding subject, medical codes 224 from acquired data elements associated with the corresponding subject, therapy/treatment codes 230 for therapies and/or treatments administered to the corresponding subject, and/or medication codes 236 for medications prescribed to the corresponding subject; and a compliance module 240 for (i) receiving a compliance request and, responsive to the compliance request, providing compliance information in accordance with a compliance counter or the noncompliance counter, (ii) providing one or more suggested treatment options based upon the health care provider compliance information, and/or (iii) providing a list of subjects that are deemed to lack a specific therapy or a treatment that is standard of care for subjects having one or more characteristics associated with the list of subjects.

In some embodiments, the insulin regimen timing module 204 is accessible within any browser (phone, tablet, laptop/desktop). In some embodiments the health system module 204 and/or compliance module 240 runs on native device frameworks, and is available for download onto the health care system 250 running an operating system 202 such as Android or iOS.

In some implementations, one or more of the above identified data elements or modules of the health care system 250 for determining health care provider monitoring compliance are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a health care system 250 for determining health care provider monitoring compliance is a smart phone (e.g., an iPHONE), laptop, tablet computer, desktop computer, or other form of electronic device (e.g., a gaming console). In some embodiments, the health care system 250 is not mobile. In some embodiments, the health care system 250 is mobile.

FIG. 3 provides a description of a data collection device 200 that can be used with the instant disclosure. The data collection device 200 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the data collection device 200 (e.g., a touch-sensitive surface such as a touch-sensitive display system 282 of the data collection device 200), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The data collection device 200 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the data collection device 200 and/or for determining an amount of physical exertion by the subject.

It should be appreciated that the data collection device 200 illustrated in FIG. 3 is only one example of a multifunction device that may be used for collecting data elements 208 from the medical device(s) 102 of a corresponding subject in a plurality of subjects, and that the data collection device 200 optionally has more or fewer components than shown, optionally combines two or more components, or optionally has a different configuration or arrangement of the components. In fact, as discussed above, in some embodiments, the data elements 208 are acquired by the health care system 250 directly from the medical devices 102 without reliance on the data collection device 200. The various components shown in FIG. 3 are implemented in hardware, software, firmware, or a combination thereof, including one or more signal processing and/or application specific integrated circuits.

Memory 192 of the data collection device 200 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the data collection device 200, such as CPU(s) 274 is, optionally, controlled by the memory controller 368.

In some embodiments, the memory 192 of the data collection device 200 illustrated in FIG. 3 includes an instance of the health system module 204 described in conjunction with FIG. 2 above. In some such embodiments, the functionality of the instance health system module 204 installed on the data collection device 200 is limited to those that pertain to a corresponding single subject (e.g., single patient) associated with the data collection device 200.

In some embodiments, the memory 192 of the data collection device 200 illustrated in FIG. 3 includes acquired data elements 206 described in conjunction with FIG. 2 above. In some such embodiments, the acquired data elements 206 in the data collection device 200 are limited to those that are from the medical device(s) 102 associated with (e.g., implanted in) a corresponding single subject (e.g., single patient) associated with the data collection device 200.

In some embodiments, the memory 192 of the data collection device 200 illustrated in FIG. 3 includes an alerts module 242 that specifies one or more alert rule 244 and for each such respective alert rule 244, an alert response 246 that is fired when for the trigger conditions for the respective alert rule 244 are fired.

In some embodiments, the data elements 208 of FIG. 3 comprise a plurality of physiological measurements, and each such physiological measurement includes a measurement value. In some embodiments, the physiological measurement is body temperature of the subject. In some embodiments, the physiological measurement is a measurement of activity of the subject. In some embodiments, these physiological measurements serve as additional data, in addition to that provided by the measurement devices 102 that is found in acquired data elements 206 associated with a subject. In some embodiments, these physiological measurements serve to verify or help to determine the condition of the corresponding subject in conjunction with the data from the measurement devices 102. In some embodiments, the optional accelerometer 317, optional GPS 319, and/or magnetometer (not shown) of the data collection device 200 or such components optionally within the one or more medical devices 102 is used to acquire such physiological measurements.

The peripherals interface 370 can be used to couple input and output peripherals of the device to CPU(s) 274 and memory 192. The one or more processors 274 run or execute various software programs and/or sets of instructions stored in memory 192, such as the health system module 204, to perform various functions for the data collection device 200 and to process data.

In some embodiments, the peripherals interface 370, CPU(s) 274, and memory controller 368 are, optionally, implemented on a single chip. In some other embodiments, they are implemented on separate chips.

RF (radio frequency) circuitry of network interface 284 receives and sends RF signals, also called electromagnetic signals. In some embodiments, the data elements 206 are received using this RF circuitry from one or more devices such as a medical device 102 associated with a subject. In some embodiments, the RF circuitry 284 converts electrical signals to/from electromagnetic signals and communicates with communications networks and other communications devices, medical devices 102 and/or the health care system 250 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the data collection device 200. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the data collection device 200 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the data collection device 200, opposite the display 282 on the front of the data collection device 200, so that the input 280 is enabled for use as a viewfinder for still and/or video image acquisition. In some embodiments, another optical sensor 373 is located on the front of the data collection device 200 so that the subject's image is obtained (e.g., to verify the health or condition of the subject, to determine the physical activity level of the subject, to help diagnose a subject's condition remotely, or to acquire visual physiological measurements 312 of the subject, etc.).

As illustrated in FIG. 2, a data collection device 200 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the data collection device 200 is a smart phone. In other embodiments, the data collection device 200 is not a smart phone but rather is a tablet computer, desktop computer, emergency vehicle computer, or other form or wired or wireless networked device. In some embodiments, the data collection device 200 has any or all of the circuitry, hardware components, and software components found in the health care system 250 depicted in FIG. 3. In the interest of brevity and clarity, only a few of the possible components of the data collection device 200 are shown in order to better emphasize the additional software modules that are installed on the data collection device 200.

Now that details of a system 48 for determining health care provider monitoring compliance have been disclosed, details regarding a flow chart of processes and features of the system, in accordance with an embodiment of the present disclosure, are disclosed with reference to FIGS. 4A through 4I. In some embodiments, such processes and features of the system are carried out by the health system module 204 and/or compliance module 240 illustrated in FIGS. 2 and 3.

Block 402.

Figure 4A:
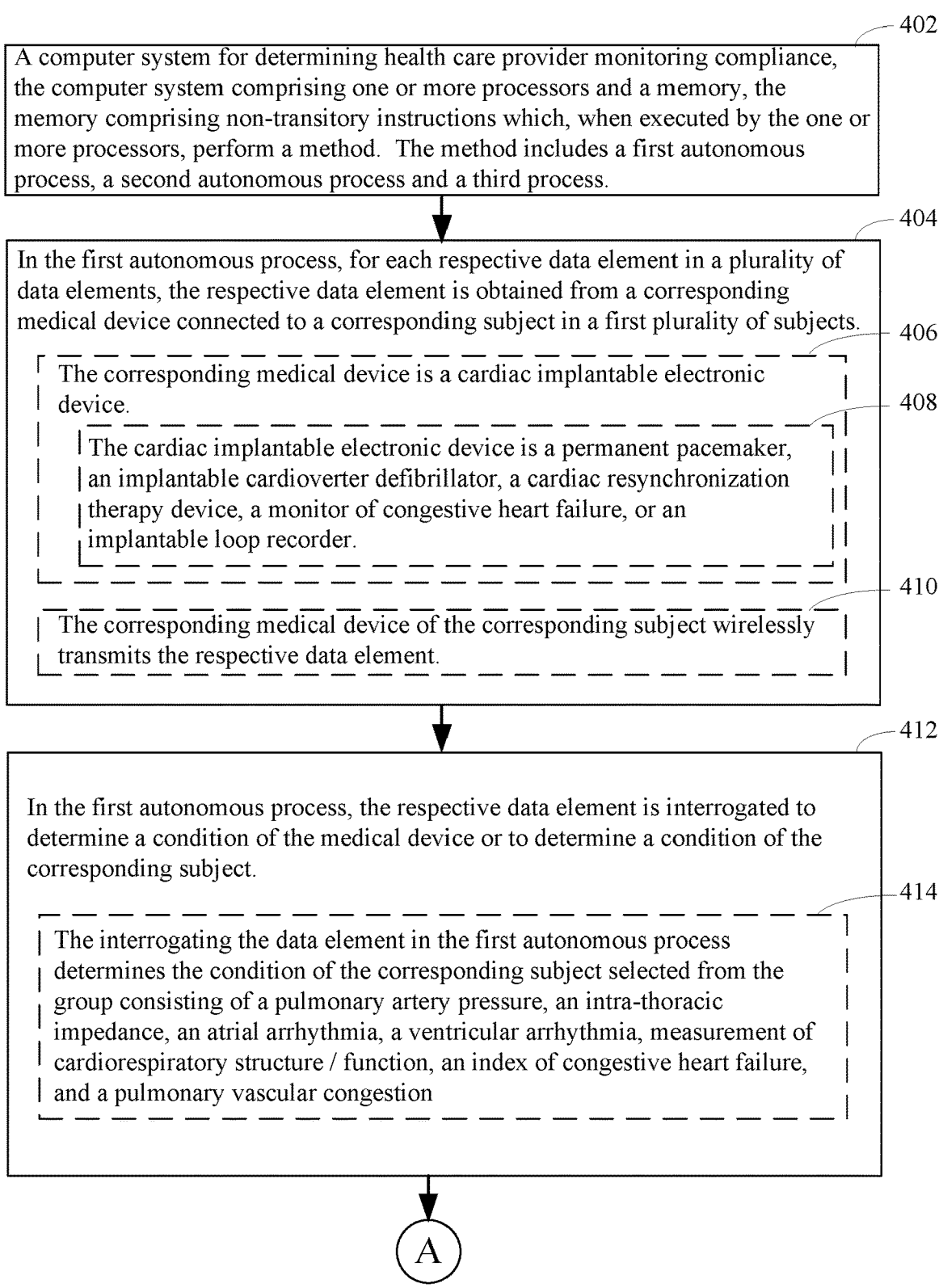

With reference to block 402 of FIG. 4A, the goal of embodiments of the present disclosure is to determine health care provider monitoring compliance. As illustrated in FIG.

2, a health care system 250 comprises one or more processors 274 and a memory 192/290. The memory stores instructions that, when executed by the one or more processors, perform a method. The method includes a first autonomous process, a second autonomous process, and a third process. Each of these processes is described in turn below.

Blocks 404-440—the First Autonomous Process.

Referring to FIG. 4A, in the first autonomous process, for each respective data element 208 in a plurality of data elements, the respective data element 208 is obtained from a corresponding medical device 102 of a corresponding subject in a first plurality of subjects. FIG. 2 illustrates. In typical embodiments, each respective data element 208 is timestamped to represent when the respective data element was made, that is, when the measurements 214 or conditions 212 contained within respective data element 208 were taken. In typical embodiments, such measurements 214 or conditions are measured by the medical device 102 without human intervention. That is, the subject does not manually make the measurements in the data element 208.

Block 404.

Referring to FIG. 4A, in the first autonomous process, for each respective data element 208 in a plurality of data elements, the respective data element 208 is obtained from a corresponding medical device 102 of a corresponding subject in a first plurality of subjects.

In some embodiments, the corresponding medical device 102 is a cardiac implantable electronic device (block 406). In some such embodiments, the cardiac implantable electronic device is a permanent pacemaker, an implantable cardioverter defibrillator, a cardiac resynchronization therapy device, a monitor of congestive heart failure, or an implantable loop recorder (block 408).

In some embodiments, the corresponding medical device 102 of the corresponding subject wirelessly transmits the respective data element 208 (block 410). For instance, in some embodiments the corresponding medical device 102 transmits the data element 208 to the data collection device 200. In some embodiments, the corresponding medical device 102 transmits the data element 208 directly to the health care system 250. Correspondingly, in some embodiments the data collection device 200 or the health care system transmits (e.g., wirelessly) all or a portion of their medical record 218 (e.g., an individual subject's compliance track record and any specific considerations/recommendations for improved standard of care (Tx or Rx or recommended diagnostic testing) back into the subject's medical device 102. This feature advantageously eases office follow up so the data is readily available and a separate interface is not required during the subject encounter with a medical practitioner. In some such embodiments, the present disclosure encompasses a new novel graphical user interface that incorporates both the usual device/programmer data coupled with the aforementioned compliance data is used in this regard. Such an application, where the individual subject compliance data is available when interrogating the medical device 102, is helpful as it is data that can be communicated to anyone who may encounter the subject without access to the compliance graphical user interface illustrated, for example in FIG. 9, that may only be available in certain medical offices (e.g., in medical network offices). For example an out of network emergency room interrogating a given subject's medical device as a result of a medical emergency or otherwise would benefit from having the data accessible using a conventional programmer for the given device.

In the first autonomous process, the respective data element 208 is interrogated to determine a condition of the medical device 102 or to determine a condition of the corresponding subject (block 412). As discussed above in conjunction with FIG. 2, in some embodiments, the data element includes identifying information, such as a medical device identifier 210. In some embodiments, the medical device identifier 210 can be used to look up an identity of the corresponding subject through a medical device registry. In some embodiments the data element include includes identity of the corresponding subject. In some embodiments the data element includes device diagnostic conditions 212. In some embodiments the data element includes medical device measurements 214.

Examples of medical device measurements 214 of the corresponding subject made by a medical device 102 include, but are not limited to, a pulmonary artery pressure, an intra-thoracic impedance, an atrial arrhythmia, a ventricular arrhythmia, measurement of cardiorespiratory structure/function, an index of congestive heart failure, or a pulmonary vascular congestion (block 414).

Figure 4B:
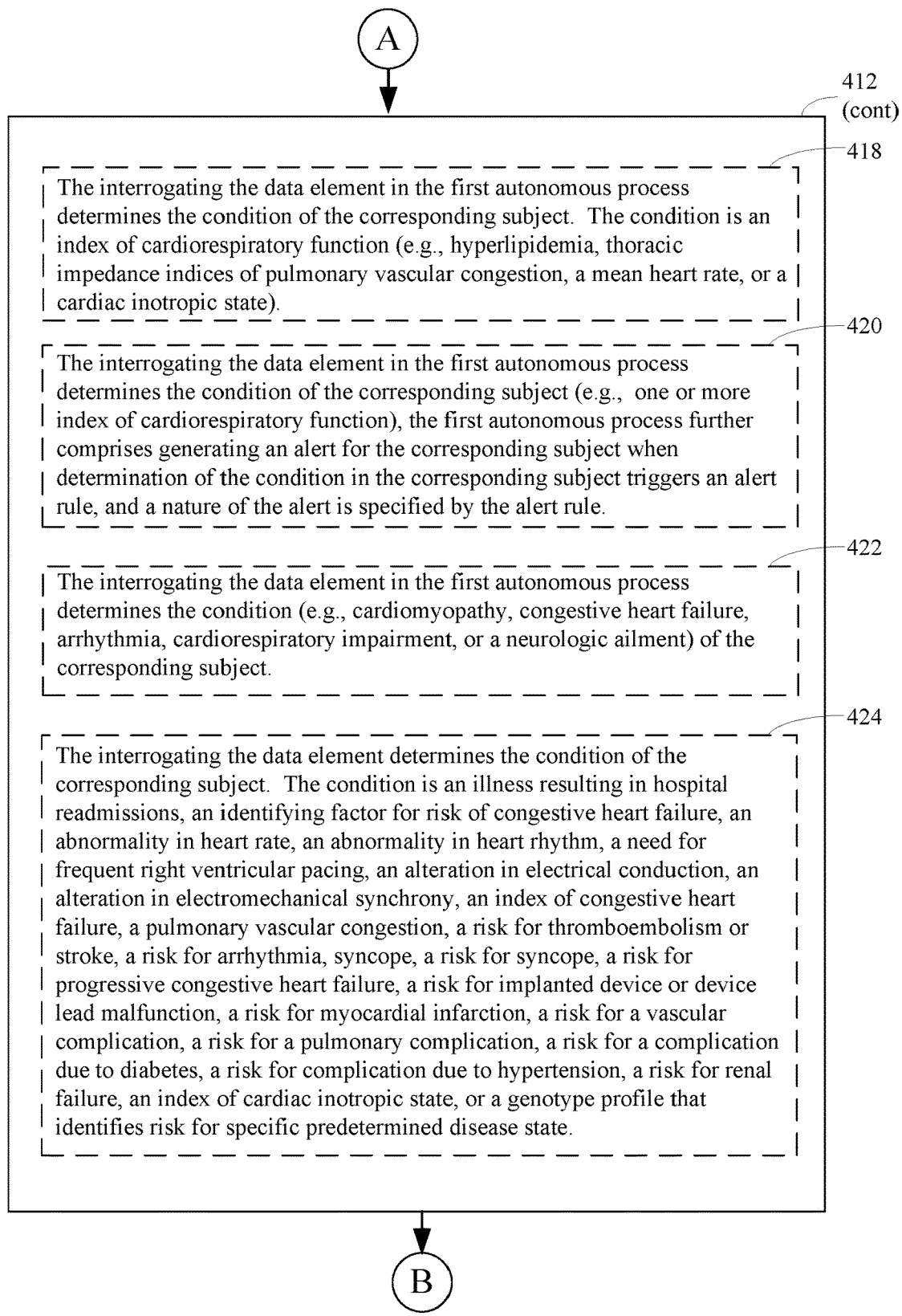

Referring to block 418 of FIG. 4B, in some embodiments, the interrogating the data element 208 in the first autonomous process determines the condition of the corresponding subject (medical device measurement 214), where the condition is an index of cardiorespiratory function (e.g., hyperlipidemia, thoracic impedance indices of pulmonary vascular congestion, a mean heart rate, or a cardiac inotropic state). Referring to block 420 of FIG. 4B, in some embodiments, the interrogation of the data element 208 in the first autonomous process determines the condition of the corresponding subject (e.g., one or more index of cardiorespiratory function) (medical device measurement 214). In some such embodiments, the first autonomous process further comprises generating an alert (alert response 246) for the corresponding subject when a determination that the condition in the corresponding subject triggers an alert rule 244, where a nature of the alert response 246 is specified by the alert rule 244. In some such embodiments, the alert response 246 is a communication of the condition that generated the alert to a delegated medical personnel. In some embodiments, an alert response 246 is a notification to the subject, through the health system module 204, for follow up care or appointment scheduling with a medical practitioner. In some embodiments, firing of an first rule comprises initiating an alert response 246 that is a visual alert response, an audible alert response or a vibrational alert response (e.g., vibrating a smart phone associated with the subject). As illustrated in FIG. 3, in an example embodiment, a data collection device 200 includes an alerts module 242 for a subject that comprises a plurality of alert rules 244, each respective alert rule 244 in the alert module 242 comprising one or more trigger conditions 230 and one or more actions responses. Each alert rule 244 comprises one or more corresponding trigger conditions and an alert response 246 a plurality of alert responses. In some embodiments, the alert module 242 compares the medical device diagnostic conditions 212 and/or medical device measurements 214 of the data elements 208 from a medical device 102 associated with a subject on a temporal ongoing basis with each trigger condition of each alert rule in the alerts module 242 and, when the medical device diagnostic conditions 212 and/or medical device measurements 214 of the data elements 208 from a medical device 102 matches trigger condition(s) of a respective alert rule 244 in the plurality of alert rules 244, the corresponding alert response 246 of the respective alert rule 244 is fired. In one example of this, the trigger condition for a first respective alert rule 244 is a drop in the blood pressure of a subject by a predetermined amount over a predetermined amount of time, and the respective alert response 246 is a notification to the user, through the alerts module 242 and/or heath system module 204 for follow up care or appointment scheduling with a medical practitioner. In some embodiments, firing of an alert rule 244 comprises initiating an alert response 246 that is a visual alert, an audible alert or a vibrational alert.

As an additional example of an alert rule 244, in some embodiments, subject symptom scores may identify a subject with a change in the severity of their disease that will trigger a pop-up or emailed alert response 246 to contact their provider and discuss the change in symptoms. As another example of an alert rule 244, automated alert responses 246 to providers will be triggered for patients "not doing well" on the basis of their health assessments, providing opportunities for intervention such as recommending an office visit sooner than scheduled.

In some embodiments, the interrogating the data element 208 in the first autonomous process determines the condition (e.g., cardiomyopathy, congestive heart failure, arrhythmia, cardiorespiratory impairment, or a neurologic ailment) (medical device measurement 214) of the corresponding subject (block 422).

Referring to block 424 of FIG. 4C, in some embodiments, the interrogation of the data element 208 determines the condition (medical device measurement 214) of the corresponding subject. In some such embodiments, the condition is an illness resulting in hospital readmissions, an identifying factor for risk of congestive heart failure, an abnormality in heart rate, an abnormality in heart rhythm, a need for frequent right ventricular pacing, an alteration in electrical conduction, an alteration in electromechanical synchrony, an index of congestive heart failure, a pulmonary vascular congestion, a risk for thromboembolism or stroke, a risk for arrhythmia, syncope, a risk for syncope, a risk for progressive congestive heart failure, a risk for implanted device or device lead malfunction, a risk for myocardial infarction, a risk for a vascular complication, a risk for a pulmonary complication, a risk for a complication due to diabetes, a risk for complication due to hypertension, a risk for renal failure, an index of cardiac inotropic state, or a genotype profile that identifies risk for specific predetermined disease state.

Referring to block 426 of FIG. 4C, in some embodiments, in the first autonomous process, responsive to the interrogating, there is recorded (a) a first medical code 226 that indicates that the condition of the medical device 102 or the condition of the corresponding subject has been evaluated and (b) an associated timestamp 228 for the interrogating in a medical record 218 associated with the corresponding subject. In some embodiments, the first medical code 226 is an ICD-9 code, an ICD-10 code, a Current Procedure Terminology (CPT) code, or an equivalent thereof (block 428).

In some embodiments, the medical record 218 is an electronic medical record (block 432). An electronic medical record refers to the systematized collection of electronically-stored health information in a digital format for a subject. This record can be shared across different health care settings. Electronic medical records are shared through network-connected, enterprise-wide information systems or other information networks and exchanges. In some embodiments, electronic medical records include a range of data, including demographics, medical history, medication and allergies, immunization status, laboratory test results, radiology images, vital signs, personal statistics like age and weight, and billing information. As used herein, the terms electronic health record and electronic medical record are used interchangeably.

In some embodiments, the first medical code 226 is a Current Procedure Terminology (CPT) code 93294, 93295, 93296, 93297, 93298, 93299, 93279, 93280, 93281, 93282, 93283, 93284, 93285, 93288, 93289, 93290 or an equivalent thereof (block 434). A description of these codes is provided in Example 1 below.

In some embodiments, the first medical code 226 is representative of one or more of an in office interrogation, reprogramming, fitting or adjustment of the corresponding medical device 102 or a remote monitoring evaluation of the corresponding medical device 102 (block 436).

In some embodiments, the first medical code 226 is ICD-10 code Z95.0, Z45.018, Z95.810, Z45.02, or an equivalent thereof (block 438).

In some embodiments, the first medical code 226 is ICD-10 code I63.4, I63.40, I63.41, I63.411, I63.412, I63.413, I63.419, I63.42, I63.421, I63.422, I63.423, I63.429, I63.43, I63.431, I63.432, I63.433, I63.439, I63.44, I63.441, I63.442, I63.443, I63.449, I63.49, I63.1, I63.10, I63.11, I63.111, I63.112, I63.113, I63.119, I63.12, I63.13, I63.131, I63.132, I63.133, I63.139, I63.19, I63.9, or an equivalent thereof (block 440).

Blocks 442-494—the Second Autonomous Process.

Referring to block 442 of FIG. 4D, the second autonomous process is performed at each respective epoch in a plurality of epochs and comprises, for each respective subject in a second plurality of subjects, a determination as to whether the first medical code 226 has been recorded in the medical record 218 associated with the respective subject during the respective epoch. This is done by parsing the medical record 218 for the first medical code 226 and, when found in the medical record 218, using the associated timestamp (medical code time stamp 228) to determine if the first medical code 226 is associated with respective epoch. For instance, consider the case where a respective epoch is the first two weeks of July in a given year. If the medical code time stamp 228 falls into the first two weeks of July of the given year, the corresponding medical code 226 is deemed to be associated with the respective epoch. On the other hand, if the medical code timestamp 228 falls outside (before or after) the first two weeks of July of the given year, the corresponding medical code 226 is deemed to not be associated with the respective epoch. The first plurality of subjects constitutes all or a portion of the second plurality of subjects and each subject in the second plurality of subjects has an implanted medical device 102. In other words, in typical embodiments the first plurality of subjects is a subset of the second plurality of subjects—those subjects in the second plurality of subjects that have an implanted medical device 102. In some such embodiments, the second plurality of subjects represents all the subjects associated with a physician, a provider group, a hospital, a hospital network, a health insurance company, a pharmacy, a governmental body or a prescribing clinician and the first plurality of subjects are those subjects associated with the physician, the provider group, the hospital, the hospital network, the health insurance company, the pharmacy, the governmental body, or the prescribing clinician that have an implanted medical device 102. In some embodiments, the first plurality of subjects is 100 or more subjects, 200 or more subjects, 1000 or more subjects, 10,000 or more subjects or 100,000 or more subjects. In some embodiments, the second plurality of subjects is 100 or more subjects, 200 or more subjects, 1000 or more subjects, 10,000 or more subjects or 100,000 or more subjects.

In some embodiments, the first medical code 226 is extracted from the context of the medical record 218 thereby providing semantic interoperability without specific reliance on a coding standard (block 443). That is, in some embodiments, the first medical code 226 is not literally in the medical record 218 but is determined by the health system module 204 from the context of the medical record (e.g., other information in the medical record). In such embodiments, the health system module 204 can make a call regarding whether the medical procedure or diagnostic test associated with the medical code 226 has been performed and when it was performed. For instance, in some such embodiments, the health system module 204 employs optical recognition technology and/or handwriting interpretation technology of the medical record 218 of a subject and the like to ascertain what service or tests were performed for the subject or the subject's medical device 102.

Referring to block 444 of FIG. 4D, in some embodiments, each corresponding medical device 102 is a pacemaker implanted in a corresponding subject. In some such embodiments, the second autonomous process further comprises identifying the second plurality of subjects by scanning the medical record 218 associated with each subject in a third plurality of subjects for a second code. In some embodiments, the second plurality of subjects is all or a portion of the third plurality of subjects. In some such embodiments, the third plurality of subjects represents all the subjects associated with a physician, a provider group, a hospital, a hospital network, a health insurance company, a pharmacy, a governmental body, or a prescribing clinician and the second plurality of subjects are those subjects associated with the physician, the provider group, the hospital, the hospital network, the health insurance company, the pharmacy, the governmental body, or the prescribing clinician that have a second code in their medical record 218. In some such embodiments, the second plurality of subjects is 100 or more subjects, 200 or more subjects, 1000 or more subjects, 10,000 or more subjects or 100,000 or more subjects. In some such embodiments, the third plurality of subjects is 100 or more subjects, 200 or more subjects, 1000 or more subjects, 10,000 or more subjects or 100,000 or more subjects. In some such embodiments, the second code is ICD-10 Z95.0, ICD-10 Z45.018, CPT 93279, CPT 93280, or CPT 93281 (or an equivalent thereof) and the first code is CPT 93294 or CPT 93296 (or an equivalent thereof).

Referring to block 446 of FIG. 4D, in some embodiments, each corresponding medical device 102 is a defibrillator implanted in a corresponding patient. The second autonomous process further comprises identifying the second plurality of subjects by scanning the medical record 218 associated with each subject in a third plurality of subjects for a second code. The second plurality of subjects is all or a portion of the third plurality of subjects. In some embodiments, the second plurality of subjects is all or a portion of the third plurality of subjects. In some such embodiments, the third plurality of subjects represents all the subjects associated with a physician, a provider group, a hospital, a hospital network, a health insurance company, a pharmacy, a governmental body, or a prescribing clinician and the second plurality of subjects are those subjects associated with the physician, the provider group, the hospital, the hospital network, the health insurance company, the pharmacy, the governmental body, or the prescribing clinician that have a second code in their medical record 218. In some such embodiments, the second plurality of subjects is 100 or more subjects, 200 or more subjects, 1000 or more subjects, 10,000 or more subjects or 100,000 or more subjects. In some such embodiments, the third plurality of subjects is 100 or more subjects, 200 or more subjects, 1000 or more subjects, 10,000 or more subjects or 100,000 or more subjects. In some such embodiments, the second code is ICD-10 Z95.810, Z45.02, CPT 93282, CPT 93283, or 93284 (or an equivalent thereof) and the first code is CPT 93295 or 93296 (or an equivalent thereof).

Referring to block 448 of FIG. 4D, in some specific embodiments, the interrogating the data element 208 in the first autonomous process determines the condition of the corresponding subject, where the condition is an index of cardiorespiratory function, and each respective epoch in the plurality of epochs used by the second process is a day. Thus, in such embodiments, the second autonomous process examines the respective medical records of each subject in the second plurality of subjects on a daily basis to see if the first process (or some other source) has added the first medical code to a medical record.

Referring to block 450 of FIG. 4D, in some embodiments, each respective epoch in the plurality of epochs is the same length of time. In other words, in such embodiments the second autonomous process is performed on a repeating basis such as every hour, every day, every two days, each week, each month, each quarter or some other length of time. In some embodiments the length of time is an hour or less, a day or less, two days or less, a week or less, a month or less, or a quarter of a year or less.

Referring to block 452 of FIG. 4D, in some embodiments, the first autonomous process and the second autonomous process occur concurrently (block 452). In such embodiments, a plurality of data elements may be obtained and processed by the first autonomous process in the manner described above, while at the same time, the second autonomous process is parsing medical records to determine whether they contain the first medical code. In some such embodiments, the second autonomous process is checking the medical records for any of a plurality of medical codes while the first autonomous process concurrently runs.

Referring to block 454 of FIG. 4E, in some embodiments, the second plurality of subjects is associated with a physician, a provider group, a hospital, a hospital network, a health insurance company, a pharmacy, a governmental body (e.g., the United States Food and Drug Administration, the United States National Institute of Health, the United States Center for Disease Control, a state health agency, a city health department, a county health department, etc.), or a prescribing clinician. Thus, for example, if the second plurality of subjects is associated with a physician, the second process checks the medical records of each subject that has a medical device 102 and that is seen by the physician. As another example, if the second plurality of subjects is associated with a health insurance company, the second process checks the medical records of each subject that has a medical device 102 and that is insured by the health insurance company.

Referring to block 456 of FIG. 4E, in some embodiments, the second plurality of subjects is associated with a physician, a provider group, a hospital, a hospital network, a health insurance company, a pharmacy, a governmental body or a prescribing clinician. Further, each subject in the second plurality of subjects has a pathologic condition (e.g., cardiomyopathy, congestive heart failure, arrhythmia, a cardiorespiratory impairment, or a neurologic ailment). The interrogating the data element 208 in the first autonomous process determines a condition of the medical device 102. The corresponding medical device 102 is of the corresponding subject and wirelessly transmits the respective data element 102. In some such embodiments, the corresponding medical device is implanted in the corresponding subject. In some such embodiments, the corresponding medical device 102 wirelessly transmits the respective data element 102 to a data collection device 200 associated with the subject. In some such embodiments, the corresponding medical device 102 wirelessly transmits the respective data element 102 directly to the health care system 250.

Referring to block 458 of FIG. 4E, in some embodiments, the second plurality of subjects is associated with a physician, a provider group, a hospital, a hospital network, a health insurance company, a pharmacy, a governmental body, or a prescribing clinician. Further, each subject in the plurality of subjects has cardiomyopathy or congestive heart failure. The interrogating the data element 208 in such embodiments in the first autonomous process determines the condition of the corresponding subject. The condition is a pathologic condition (e.g., cardiomyopathy, congestive heart failure, arrhythmia, a cardiorespiratory impairment, a neurologic ailment, etc.). The corresponding medical device 102 of the corresponding subject wirelessly transmits the respective data element 208. In some embodiments, the corresponding medical device is implanted in the corresponding subject. In some such embodiments, the corresponding medical device 102 wirelessly transmits the respective data element 102 to a data collection device 200 associated with the subject. In some such embodiments, the corresponding medical device 102 wirelessly transmits the respective data element 102 directly to the health care system 250.

Referring to block 460 of FIG. 4E, in some embodiments, the second plurality of subjects is associated with a physician, a provider group, a hospital, a hospital network, a health insurance company, a pharmacy, a governmental body, or a prescribing clinician. Further, each subject in the second plurality of subjects has been diagnosed with an ailment. Each subject in the second plurality of subjects has been coded for hospital readmission for the ailment. Thus, in such embodiments, the second autonomous process checks the medical records of only those subjects that have been coded for hospital readmission for the ailment.

Referring to block 462 of FIG. 4F, in some embodiments the second plurality of subjects is associated with a physician, a provider group, a hospital, a hospital network, a health insurance company, a pharmacy, a governmental body, or a prescribing clinician. Each subject in the second plurality of subjects satisfies a set of screening criteria. In some such embodiments, the set of screening criteria comprises: (i) historical tobacco use, (ii) male, and (iii) over 65 years of age, the interrogating the data element 208 in the first autonomous process determines a condition of the corresponding subject, and the condition is whether a predetermined treatment regimen has been performed on the corresponding subject (block 464). In some embodiments, the set of screening criteria comprises 2, 3, 4, 5, 6, 7, 8, 9, 10, or more criteria, the interrogating the data element 208 in the first autonomous process determines a condition of the corresponding subject, and the condition is whether a predetermined treatment regimen has been performed on the corresponding subject (block 466).

Referring to block 468 of FIG. 4F, in some embodiments, the second autonomous process further comprises identifying the second plurality of subjects by scanning the medical record 218 associated with each subject in a third plurality of subjects for a second code. In such embodiments, the second plurality of subjects is all or a portion of the third plurality of subjects. In other words, in typical embodiments, the second plurality of subjects is a subset of the third plurality of subjects. In some such embodiments, the second code is ICD-10 144.7, ICD-10 Z95.810, CPT 93282, or CPT 93283, and the first code is CPT 93284.

Referring to block 470 of FIG. 4F, in some embodiments the second autonomous process further comprises identifying the second plurality of subjects by scanning the medical record 218 associated with each subject in a third plurality of subjects for a second code. The second plurality of subjects is all or a portion of the third plurality of subjects. In other words, in typical embodiments, the second plurality of subjects is a subset of the third plurality of subjects. The second code is a combination of a first CPT code or ICD-10 code, or equivalent thereof, identifying that a subject has an implanted cardiac rhythm management device that does not include cardiac resynchronization therapy and a second CPT or second ICD-10 code, or equivalent thereof, identifying the patient as having congestive heart failure or risk for congestive heart failure. In some such embodiments, the first CPT code or ICD-10 code is ICD-10 Z95.0, ICD-10 Z45.018, ICD-10 Z45.02 or ICD-10 Z95.810 and the second CPT code or ICD-10 code is ICD-10 I44.7, ICD-10 I44.2, ICD-10 I44.3, ICD-10 I50.22, ICD-10 I50.23, ICD-10 I50.32, ICD-10 I50.42, ICD-10 I50.43, or ICD-10 I50.20 (block 472).

Referring to block 474 of FIG. 4G, in some embodiments the second autonomous process further comprises identifying the second plurality of subjects by scanning the medical record 218 associated with each subject in a third plurality of subjects for a second code. The second plurality of subjects is all or a portion of the third plurality of subjects. In other words, in typical embodiments, the second plurality of subjects is a subset of the third plurality of subjects. The second code is a CPT code identifies the patient as having cardiac resynchronization therapy. In some such embodiments, the CPT code is 93281 or 93284 (block 476).

Referring to block 478 of FIG. 4G, in some embodiments the second autonomous process further comprises identifying the second plurality of subjects by scanning the medical record 218 associated with each subject in a third plurality of subjects for a second code. The second plurality of subjects is all or a portion of the third plurality of subjects. Thus, in typical embodiments, the second plurality of subjects is a subset of the third plurality of subjects. The second code is an ICD-10 code, or equivalent thereof, identifying the patient as having cardiac resynchronization therapy. In some such embodiments, the ICD-10 code is in the I44.x or I50.yy families of ICD-10 codes, or is an equivalent thereof (block 480).

Referring to block 482 of FIG. 4G, in some embodiments each corresponding medical device 102 is an implantable loop recorder. In such embodiments, the second autonomous process further comprises identifying the second plurality of subjects by scanning the medical record 218 associated with each subject in a third plurality of subjects for a second code. The second plurality of subjects is all or a portion of the third plurality of subjects. Thus, in typical embodiments, the second plurality of subjects is a subset of the third plurality of subjects. In such embodiments, the second code is a second CPT-10 code, or equivalent thereof, that identifies a corresponding subject as having an implantable loop recorder evaluated in the office. The first code is a first CPT-10 code, or equivalent thereof, that identifies whether or not the corresponding subject's implantable loop recorder is being monitored remotely at specific time intervals. In some such embodiments, the first code is CPT-10 93298 or CPT-10 93299 (or an equivalent thereof) and the second code is CPT-10 92385 (or an equivalent thereof) (block 484).

Referring to block 486 of FIG. 4G, in some embodiments each corresponding medical device 102 is an implantable loop recorder. The second autonomous process identifies the second plurality of subjects by scanning the medical record 218 associated with each subject in a third plurality of subjects for a second code. The second plurality of subjects is all or a portion of the third plurality of subjects. Thus, in typical embodiments, the second plurality of subjects is a subset of the third plurality of subjects. The second code is within the family of ICD-10 I63.4, ICD-10 I63.1, or I63.9, or equivalent thereof. The first code is CPT 93285 or CPT 93298. In some such embodiments, the first code is CPT-10 93298 or CPT-10 93299 (or an equivalent thereof) and the second code is CPT-10 92385 (or an equivalent thereof) (block 488).

Figure 4H:
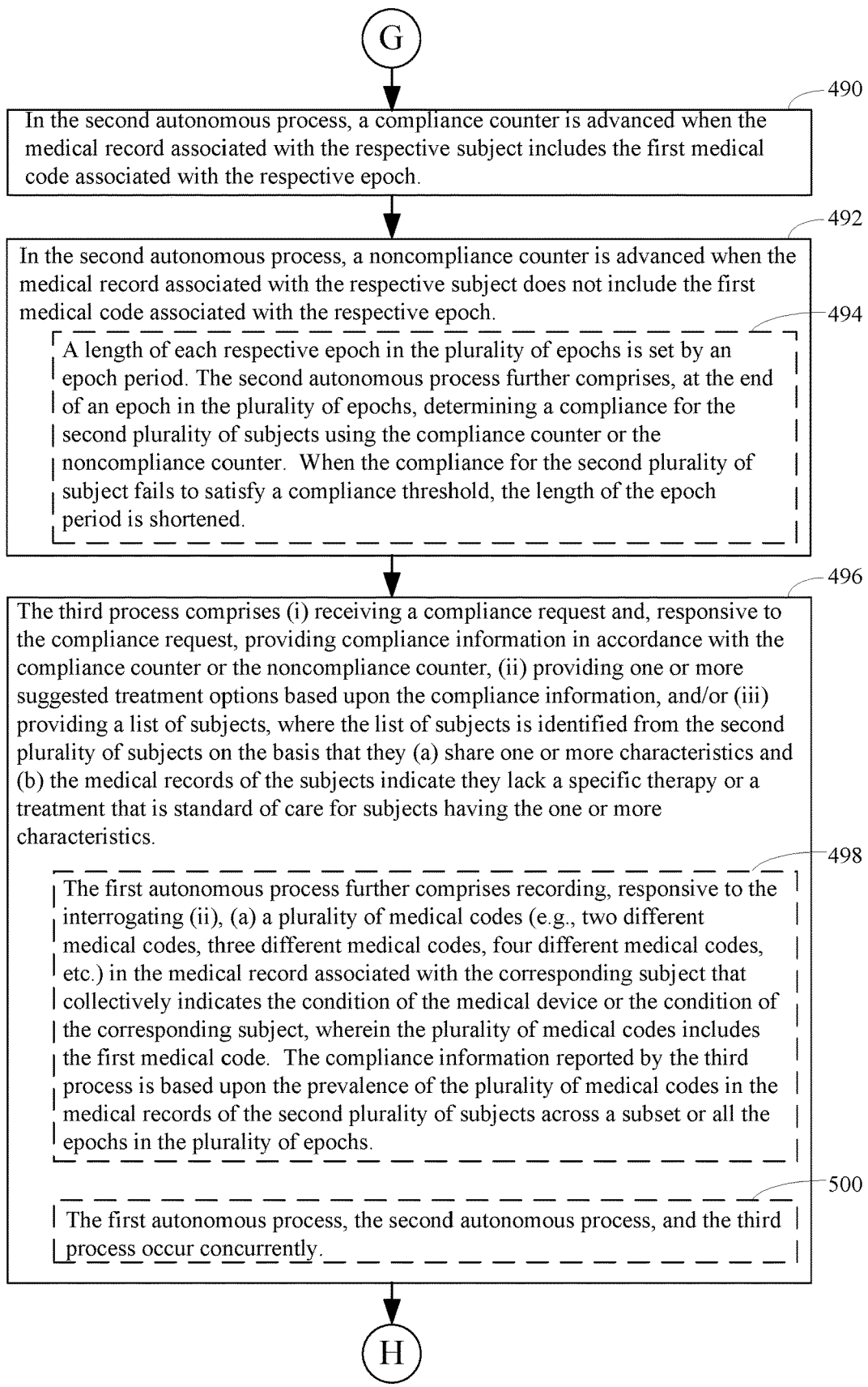
Figure 5:
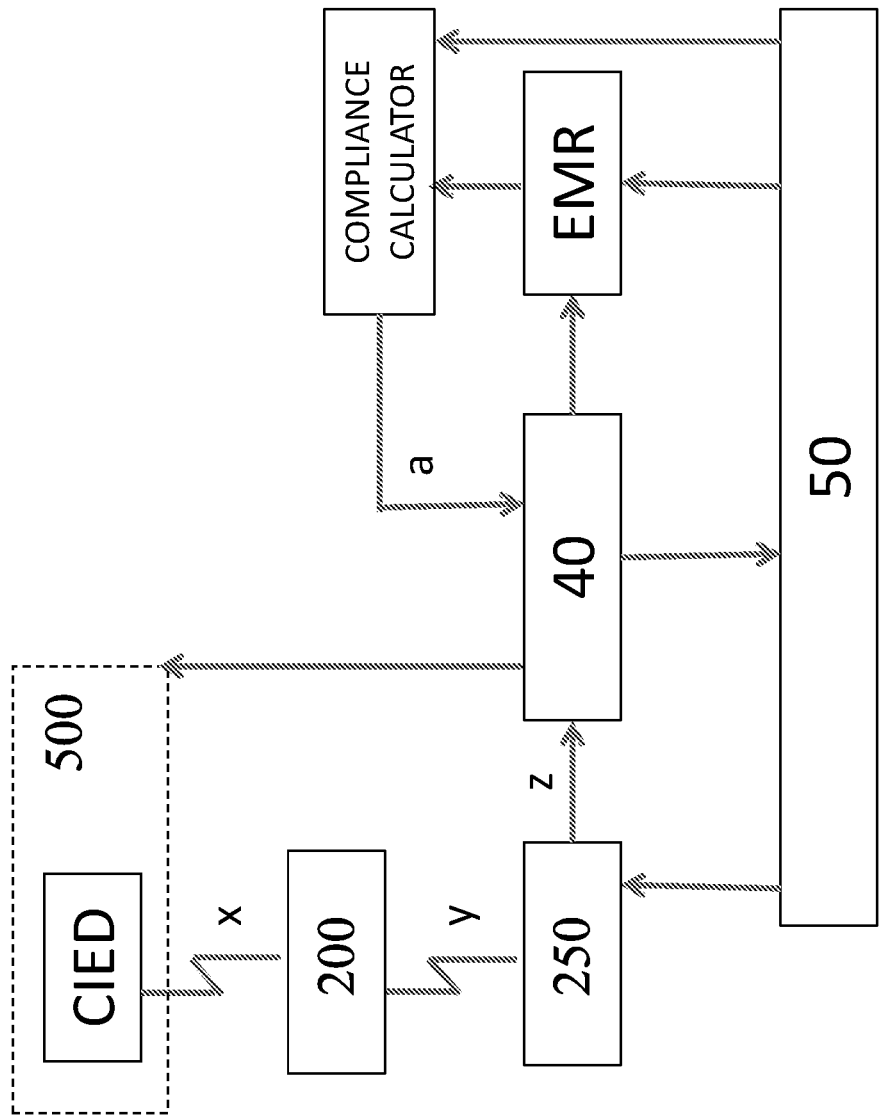
FIG. 5 depicts a flow diagram of the different components that comprise a working remote monitoring system.
Figure 6:
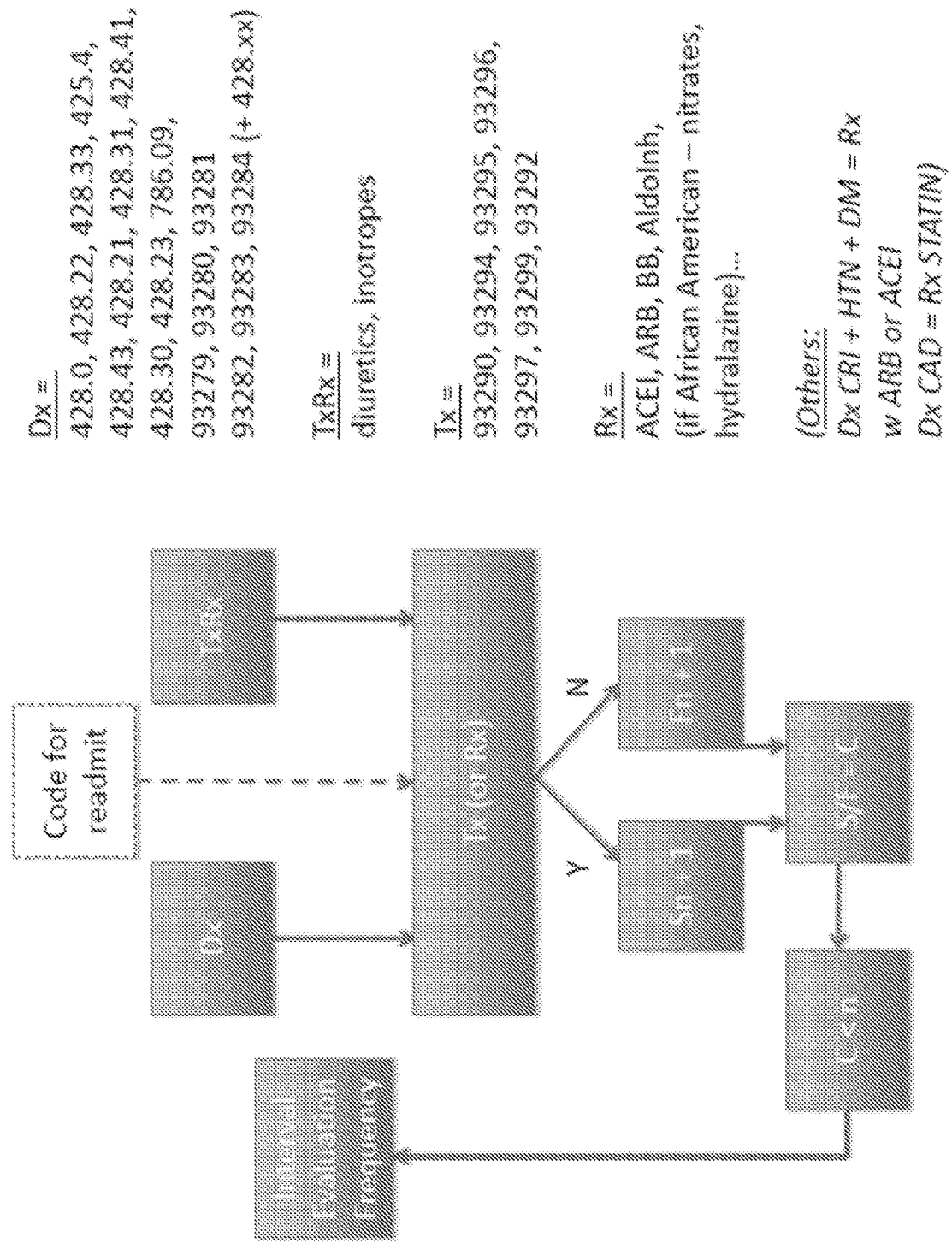
FIG. 6 depicts the workings of the compliance calculator in accordance with an embodiment of the present disclosure. Inpatient/outpatient EMR entry of diagnostic codes, Dx, or therapeutic medications, TxRx, are identified and the associated patients are monitored at Tx (or Rx). At Tx (or Rx) it is determined whether or not the individual patient has been billed/coded as having received specific treatment. By way of example, if a patient has a pacemaker or defibrillator, Dx=932xx (xx=79-84), then at Tx (or Rx) the system queries as to whether the patient has been billed for remote monitoring of their device (Tx (or Rx)=932yy (yy=99, 94-97). If yes, then Sn+1 Success counter increments by 1. If no, then Fn+1 Failure counter increments by 1. Compliance Counter C (C=successes/failures) provides an index of compliance for patient enrollment into Remote Monitoring at the specified office/hospital. The greater C is, the better the Network's compliance. If C falls below a default or programmed value then the interval evaluation frequency increases and/or an intervention is initiated. Hospital based coding for readmissions (e.g., for CM+CHF) can also be monitored, and the algorithm checks to see if the patient received the appropriate treatment (e.g., ICD implant, CardioMEMS implant, external defibrillator). Other examples can include utilization of medications for patients with CHF (482.xx), and whether or not they are on the appropriate Rx (e.g., ACEI, ARB, BB, etc.).
Figure 7:
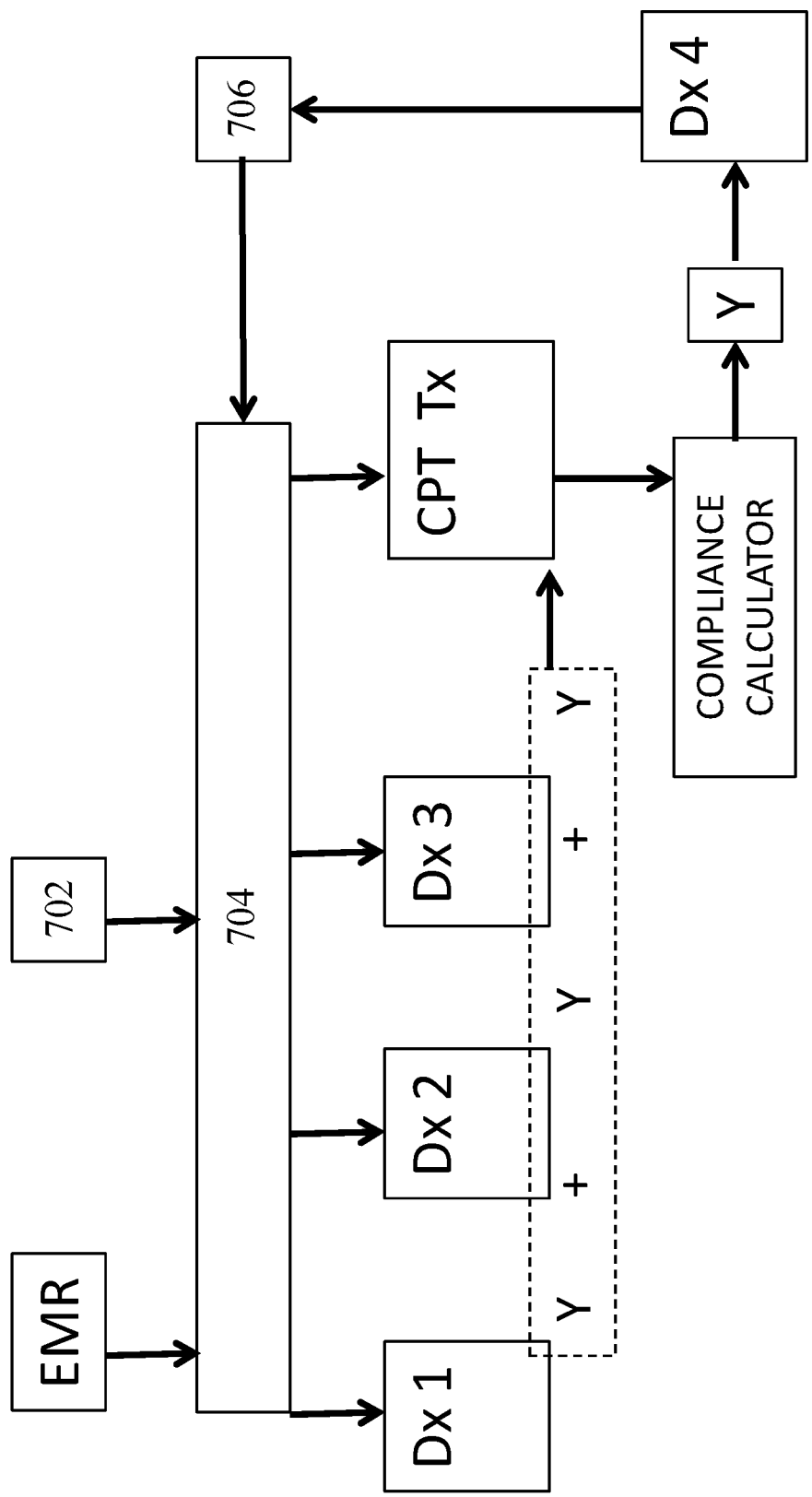
FIG. 7 relates to provider compliance ordering diagnostic testing for screening purposes or delivering appropriate, standard of care treatment, and in this example is specific for performing abdominal ultrasounds to rule out aortic aneurysms in males over the age of 65 who have a history of tobacco use. The US Preventive Services Task Force recommends screening for abdominal aortic aneurysm (AAA) by ultrasonography in men aged 65 to 75 who have ever smoked based on published randomized controlled studies of screening for AAA demonstrating that surgical repair of large AAA (greater than 5.5 cm) decreases mortality. Data from the EMR and/or other sources 702 are analyzed and fields searched using a compliance search engine 704 that queries if certain conditions, Dx 1-3 are met. By way of example, search engine 704 looks for diagnostic codes related to tobacco use at Dx 1, patient age over 65 at Dx 2 and male sex at Dx 3. Any number of conditions N can be analyzed depending on the nature of the compliance query. Search engine 704 also looks at data from other sources 702 (e.g., charges for CPT code, 76775, for abdominal aorta ultrasonography). If all conditions Dx1-DxnN are met the algorithm assesses whether a specific test (or treatment modality) has been performed at CPT Tx. If the answer is "yes" then the compliance calculator adds a value of 1 to the S (success) counter. If the answer is "no" the compliance calculator adds a value of 1 to the F (failure counter) and notifies the provider and/or patient that they have indications for testing or treatment. Any number of variables can be analyzed to determine whether or not indications are met. For example, if the patient has another condition that precludes the need for such testing or is not a candidate for testing or treatment this can be accounted for in the analysis prior to determination of compliance. In some embodiments, the search engine 704 looks for a code indicating the patient is terminal and has a do not resuscitate order in place or has end-stage heart failure and at high risk for any available treatment modality and end further queries. In this depicted example, the patient had the recommended test performed (abdominal ultrasound) and has a diagnosis detected at Dx 4, of AAA between 4 and 5.5 cm. Based on that information the system will automatically check at interval counter 706 that a repeat ultrasound of the abdominal aorta is performed every 6 months on this patient until a different condition is met (e.g., AAA>5.5 cm) and therapy is required (aneurysm repair).
Figure 8:
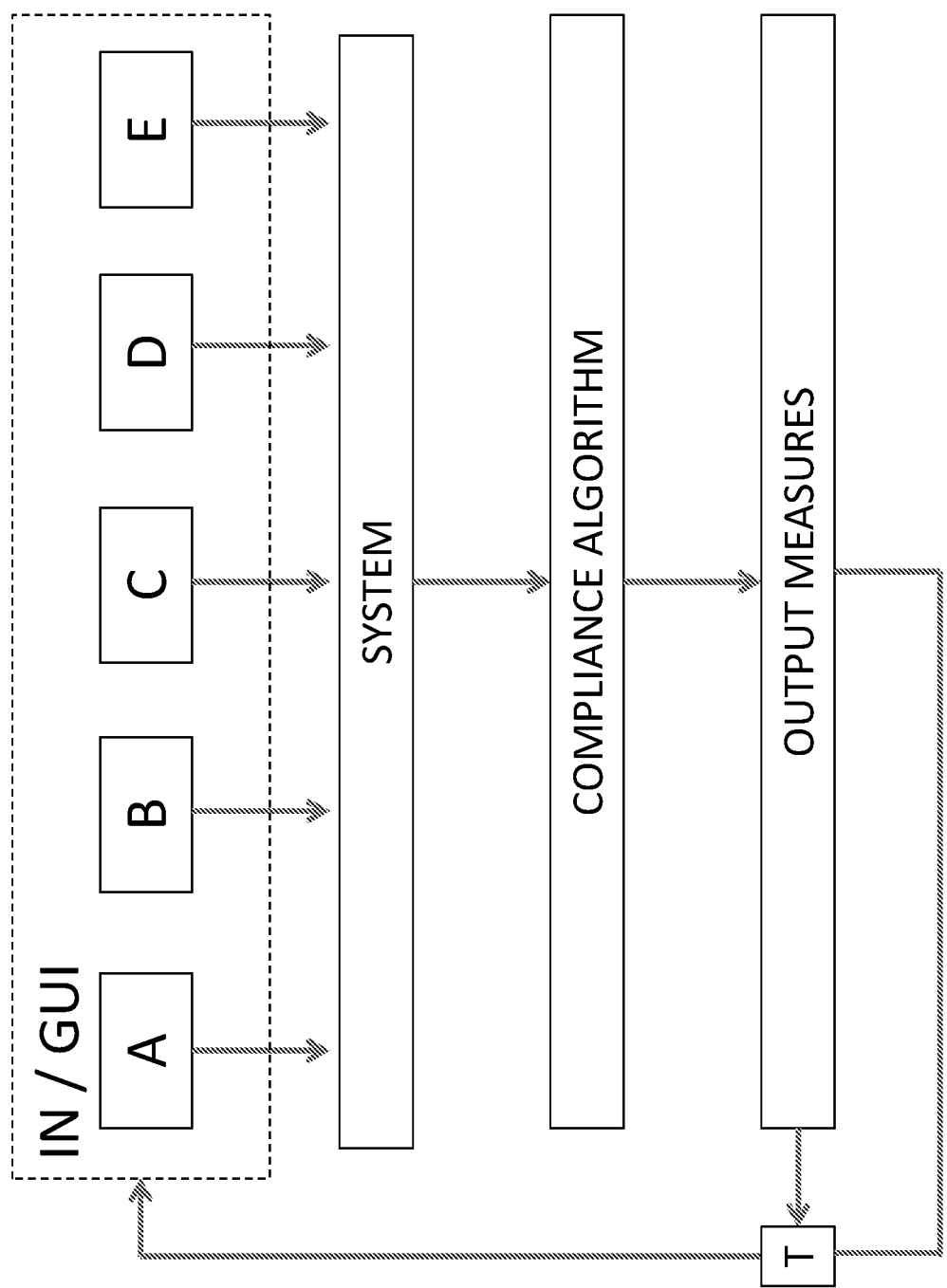
FIG. 8 demonstrates how, in one embodiment, all information is transmitted wirelessly providing for seamless system operation and communication through a simplified graphical user interface. Preferably, context management is implemented to facilitate data transmission, interface disparate applications, and provide feedback to the relevant parties in real time, where the frequency of derivation of a compliance index and timing of data presentation of such an index is determined in part by the calculated compliance index as part of a feedback loop. Elements A, B, C, D, and E, are sources of input data, IN. By way of example, "A" is the EMR, "B" is billing information, "C" is pharmacy data, "D" is a portal for a given patient, and "E" is a portal for the health care provider. All data is input into the system data bank and the compliance algorithm is applied. The data generated is then used to provide feedback to sources of input data, calculate a compliance index, and improve standard of care. Timer T controls how often the process is repeated and is affected at least in part by output data measures. In a preferred embodiment, all information is transmitted wirelessly providing for seamless system operation and communication through a simplified graphical user interface. Ideally, context management is implemented to facilitate data transmission, interface disparate applications, and provide feedback to the relevant parties in real time.

Referring to block 490 of FIG. 4H, in the second autonomous process, a compliance counter is advanced when the medical record 218 associated with the respective subject includes the first medical code 226 associated with the respective epoch. Further, referring to block 492 of FIG. 4H, in the second autonomous process a noncompliance counter is advanced when the medical record 218 associated with the respective subject does not include the first medical code 226 associated with the respective epoch. Thus, for instance, if there are 100 subjects in the second plurality of subjects and 60 of the subjects have the first medical code associated with the respective epoch and 40 of the subjects do not, the compliance counter is advanced 60 times and the noncompliance counter is advanced 40 times.

Referring to block 494, in some such embodiments, a length of each respective epoch in the plurality of epochs is set by an epoch period. The second autonomous process further comprises, at the end of an epoch in the plurality of epochs, determining a compliance for the second plurality of subjects using the compliance counter and/or the noncompliance counter. When the compliance for the second plurality of subject fails to satisfy a compliance threshold, the length of the epoch period is shortened. To illustrate, in one example the original epoch period is three months and the compliance for the second plurality of subject is deemed to fail to satisfy the compliance threshold. As a result, the epoch period is reduced to one month meaning that the second autonomous process is now run on a monthly basis until some determined event occurs (e.g., the compliance for the second plurality of subject starts to satisfy the compliance threshold).

In some embodiments, counts for the compliance counter and/or counts for the noncompliance counter that occur earlier than a set cutoff time are down-weighted relative to more recent counts that occur after the set cutoff time. For instance, consider the case where an epoch is a month and the set cutoff time is one year. In such instances, counts applied to the compliance counter and/or counts applied to the noncompliance counter from epochs occurring over a year ago are given less weight than counts applied to the compliance counter and/or counts applied to the noncompliance counter from epochs occurring less than a year ago. For instance, counts from epochs occurring more than a year ago may contribute 1× to a corresponding counter whereas counts from epochs occurring within the past year may contribute 2× to a corresponding counter. In some embodiments, such downweighting is applies as a linear function of time, a non-linear function of time, or a memory cut-off where counts older than a specific epoch are completely eliminated. An example of a non-linear downweighting could be, for example, weighing the counts in the last five epochs 100%, counts in the five epochs prior to the last five epochs 50%, and disregarding all counts from epochs before the last ten epochs when computing a respective count for the compliance counter or non-compliance counter.

The extent that counts that are occur prior to a set cutoff time used for downweighting is application dependent. In some embodiments, such counts are uniformly downweighted by a predetermined amount between zero and 99 percent, such as fifty percent.

In some embodiments, the application of the set cutoff time is applied to both the compliance counter and the noncompliance counter.

In any of the above embodiments the compliance counter and the noncompliance counter are embodied as a single first counter where this first counter is incremented for each medical record associated with a respective subject that includes the first medical code associated with the respective epoch identified by the second autonomous process (subject to downweighting and/or cutoff) and is decremented for each medical record associated with a respective subject that does not include the first medical code associated with the respective epoch (subject to downweighting and/or cutoff). In some such embodiments, there is a second counter that increments each time the first counter is either incremented or decremented thereby keeping track of the total number of medical records evaluated across a number of epochs. In such embodiments, compliance is calculated as the ratio of the first counter to the second counter.

In some embodiments, counts for the compliance counter and/or counts for the noncompliance counter that occur earlier than a set cutoff time are not included in the running compliance counter count or the running noncompliance count. For instance, consider the case where an epoch is a month and the set cutoff time is one year. In such instances, compliance/noncompliance counts from epochs occurring over a year ago are not applied to the respective compliance counter or noncompliance counter whereas counts from epochs occurring less than a year ago are applied to the respective compliance counter or noncompliance counter.

Blocks 496-526—the Third Process.

Figure 9:
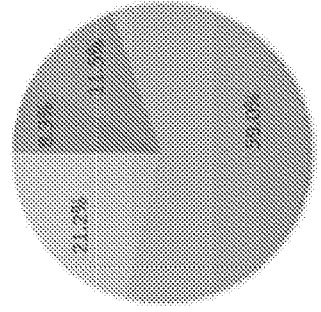
FIG. 9 illustrates an example of a process in which a compliance request is received and, responsive to the compliance request, compliance information is provided in accordance with a compliance counter or a noncompliance counter in accordance with various embodiments of the present disclosure.
Figure 9:

Referring to block 496 of FIG. 4H, the third process comprises (i) receiving a compliance request and, responsive to the compliance request, providing compliance information in accordance with the compliance counter or the noncompliance counter, (ii) providing one or more suggested treatment options based upon the compliance information, and/or (iii) providing a list of subjects, where the list of subjects is identified from the second plurality of subjects on the basis that they (a) share one or more characteristics and (b) the medical records 218 of the subjects indicate they lack a specific therapy or a treatment that is standard of care for subjects having the one or more characteristics. An example in which the third process comprises receiving a compliance request and, responsive to the compliance request, providing compliance information in accordance with the compliance counter or the noncompliance counter is illustrated in FIG. 9. In FIG. 9, responsive to a compliance request, compliance information is provided. This compliance information indicates how many subjects (patients) have been evaluated (810), and the level compliance for the patients. The report indicates, for example, that 67 patients were over 75% compliant in the past year meaning that for at least 75% of the epochs (e.g., months or some other time interval less than a year) within the past year, the first medical code (indicating that a condition of their medical device 102 or a determination of a condition of the patient has been made) is present in the medical records 218 for these 67 patients. The report further indicates, for example, that 93 patients were between 25-75% compliant in the past year meaning that for between 25-75% of the epochs (e.g., months or some other time interval less than a year) within the past year, the first medical code (indicating that a condition of their medical device 102 or a determination of a condition of the patient has been made) is present in the medical records 218 for these 93 patients. The report further indicates, for example, that 478 patients were less than 25% compliant in the past year meaning that for less than 25% of the epochs (e.g., months or some other time interval less than a year) within the past year, the first medical code (indicating that a condition of their medical device 102 or a determination of a condition of the patient has been made) is present in the medical records 218 for these 478 patients. The report further indicates, for example, that 172 patients had no monitoring in the past year meaning that the first medical code (indicating that a condition of their medical device 102 or a determination of a condition of the patient has been made), or an equivalent thereof, is not present in the medical records 218 for these 478 patients in the past year.

Referring to block 498, in some embodiments the first autonomous process further comprises recording, responsive to the interrogating of the data elements 208, (a) a plurality of medical codes (e.g., two different medical codes, three different medical codes, four different medical codes, etc.) in the medical record 218 associated with the corresponding subject that collectively indicates the condition of the medical device 102 or the condition of the corresponding subject, where the plurality of medical codes includes the first medical code. In other words, the present disclosure is not limited to recording just a first medical code as a result of the interrogation of the data elements 208. In fact, any number of relevant medical codes can be recorded in the medical records 218 due to such interrogation. In some such embodiments, the compliance information reported by the third process is based upon the prevalence of the plurality of medical codes in the medical records 218 of the second plurality of subjects across a subset or all the epochs in the plurality of epochs. That is, the compliance and noncompliance counters can track the presence (or absence) of more than one medical code across the epochs. In alternative embodiments, separate compliance and noncompliance counters are provided for each medical code of the plurality of medical codes.

Referring to block 500 of FIG. 4H, in some embodiments, the first autonomous process, the second autonomous process, and the third process occur concurrently.

Referring to block 502 of FIG. 4I, in some embodiments the second autonomous process further comprises determining whether each subject in the plurality of subjects has been prescribed a medication by parsing the medical record 218 associated with each subject in the second plurality of subjects for an indication of the medication. In some such embodiments, the medication is for a beta blocker, a lipid lowering therapy, an angiotensin converting enzyme inhibitor, an angiotensin receptor blocker, an aldosterone receptor blocker, hydralazine, a nitrate, a PCSK9 inhibitor, a negative chronotropic agent, a hyperpolarization-activated cyclic nucleotide-gated channel blocker, an anti-platelet agent, an anti-coagulant, a Neprilysin inhibitor, or a cardiac sinus node inhibitor. In some such embodiments, the presence of the indication of the medication in the medical records 218 corresponding to the second plurality of subjects contributes to the compliance information (block 504).

Referring to block 506 of FIG. 4I, in some embodiments the second autonomous process further comprises determining whether each subject in the second plurality of subjects has been prescribed a supplemental medical device by parsing the medical record 218 associated with each subject in the second plurality of subjects for a second medical code. In some such embodiments, the supplemental medical device is a cardiac rhythm management device, a cardiac rhythm management device configured to monitor or treat congestive heart failure, a heart failure treatment device, a respiratory support apparatus, a non-invasive ventilation therapy, or a continuous positive airway pressure device (block 506). In some such embodiments, the presence of the second medical code in the medical records 218 corresponding to the second plurality of subjects contributes to the compliance information (block 508). For instance, in some such embodiments, the presence of the second medical code in an epoch in the plurality of epochs causes the second autonomous process to advance the compliance counter. In another example, in some such embodiments, the presence of the second medical code in an epoch in the plurality of epochs causes the second autonomous process to advance a second compliance counter that is used in conjunction with the compliance counter for the first medical code when reporting compliance information.

Referring to block 510 of FIG. 4I, in some embodiments the second autonomous process further comprises determining whether each subject in the second plurality of subjects has been prescribed a supplemental therapy by parsing the medical record 218 associated with each subject in the second plurality of subjects for a second medical code. The supplemental therapy is non-invasive ventilation therapy. In some such embodiments, the presence of the second medical code in the medical records 218 corresponding to the second plurality of subjects contributes to the compliance information (block 512). For instance, in some such embodiments, the presence of the second medical code in an epoch in the plurality of epochs causes the second autonomous process to advance the compliance counter. In another example, in some such embodiments, the presence of the second medical code in an epoch in the plurality of epochs causes the second autonomous process to advance a second compliance counter that is used in conjunction with the compliance counter for the first medical code when reporting compliance information.

Referring to block 514 of FIG. 4J, in some embodiments the third process identifies the absence of an expected treatment or diagnostic modality or provides a suggested treatment for a subject in the first plurality of subjects when the compliance information indicates that treatment for the subject has failed a compliance threshold over the plurality of epochs.

Referring to block 516 of FIG. 4J, in some embodiments the third process identifies the absence of an expected treatment or diagnostic modality, or provides a suggested treatment for a subset of subjects in the first plurality of subjects when the compliance information indicates that treatment for the subset of subjects has failed a compliance threshold over the plurality of epochs.

Referring to block 518 of FIG. 4J, in some embodiments the respective data element in the plurality of data elements from the corresponding medical device provides a condition of the subject that is recorded in the medical record 218 associated with the subject and the third process provides a suggested treatment for the subject based upon the condition or identifies the absence of an expected treatment or diagnostic modality. In some such embodiments the condition is an irregular heartbeat and the suggested treatment regimen is a medication for the irregular heartbeat (block 520). In another example, the condition is a thoracic impedance measurement that indicates that the subject has congestive heart failure and the one or more suggested treatment options is to provide the subject with a device that provides resynchronization therapy or biventricular pacing when the subject's record indicate that they have not been provided with resynchronization therapy or biventricular pacing (block 522).

Referring to block 524 of FIG. 4J, in some embodiments, as discussed above, the compliance counter and the non-compliance counter are two separate counters. In other embodiments discussed above, the compliance counter and the noncompliance counter are a single counter (block 526).

EXAMPLE EMBODIMENTS

Example 1

In this example embodiment, a method for deriving an index of compliance is provided that is based on an input diagnostic or treatment code to determine health care provider compliance monitoring patients with implanted cardiac devices. The cardiac devices have wireless monitoring capability and connectivity to a monitoring network. In some such embodiments, the input diagnostic code is representative of one or more of an in office interrogation, reprogramming, fitting or adjustment of an implanted cardiac device or a remote monitoring evaluation of an implanted cardiac device.

In some such embodiments, the input diagnostic code is representative of a Current Procedure Terminology (CPT) code including but not limited to one of: 93294, 93295, 93296, 93297, 93298, 93299, 93279, 93280, 93281, 93282, 93283, 93284, 93285, 93288, 93289, or 93290. CPT codes are numbers assigned to every task and service a medical practitioner may provide to a patient in the United States including medical, surgical and diagnostic services. They are then used by insurers to determine the amount of reimbursement that a practitioner will receive by an insurer when the service is performed.

In some such embodiments, the input diagnostic code is CPT code 93294: remote interrogation device evaluation(s), up to 90 days, single, dual, or multiple lead pacemaker system with interim analysis, review(s) and report(s) by a physician or other qualified health care professional.

In some such embodiments, the input diagnostic code is CPT code 93295: remote interrogation device evaluation(s), up to 90 days, single, dual, or multiple lead implantable defibrillator system with interim analysis, review(s) and report(s) by a physician or other qualified health care professional.

In some such embodiments, the input diagnostic code is CPT code 93296: remote interrogation device evaluation(s), up to 90 days, single, dual, or multiple lead pacemaker system or implantable defibrillator system, remote data acquisition(s), receipt of transmissions and technician review, technical support and distribution of results.

In some such embodiments, the input diagnostic code is CPT code 93297: remote interrogation device evaluation(s), up to 30 days; implantable cardiovascular monitor system, including analysis of one or more recorded physiologic cardiovascular data elements 208 from all internal and external sensors, analysis, review(s) and report(s) by a physician or other qualified health care professional.

In some such embodiments, the input diagnostic code is CPT code 93298: remote interrogation device evaluation(s), up to 30 days; implantable loop recorder system, including analysis of recorded heart rhythm data, analysis, review(s) and report(s) by a physician or other qualified health care professional.

In some such embodiments, the input diagnostic code is representative of an ICD-10 code including but not limited to one of: Z95.0 (presence of a cardiac pacemaker), Z45.018 (encounter for adjustment and management of other part of cardiac pacemaker), Z95.810 (presence of automatic implantable cardiac defibrillator), and Z45.02 (encounter for adjustment and management of automatic implantable cardiac defibrillator).

In some such embodiments, the input diagnostic code is CPT code 93299 remote interrogation device evaluation(s), up to 30 days, implantable cardiovascular monitor system or implantable loop recorder system, remote data acquisition (s), receipt of transmissions and technician review, technical support and distribution of results.

In some such embodiments, the input diagnostic code is CPT code 93279: (implantable pacemaker) in person programming device evaluation with iterative adjustment of the implantable device to test the function of the device and select optimal permanent programmed values with physician analysis, review and report; single lead pacemaker system.

In some such embodiments, the input diagnostic code is CPT code 93280: (implantable pacemaker) in person programming device evaluation (in person) with iterative adjustment of the implantable device to test the function zf the device and select optimal permanent programmed values with physician analysis, review and report; dual lead pacemaker system.

In some such embodiments, the input diagnostic code is CPT code 93281: (implantable pacemaker) in person programming device evaluation with iterative adjustment of the implantable device to test the function of the device and select optimal permanent programmed values with physician analysis, review and report; multiple lead pacemaker system.

In some such embodiments, the input diagnostic code is CPT code 93282: (implantable cardioverter-defibrillator) in person programming device evaluation with iterative adjustment of the implantable device to test the function of the device and select optimal permanent programmed values with physician analysis, review and report; single lead implantable cardioverter-defibrillator system.

In some such embodiments, the input diagnostic code is CPT code 93283: (implantable cardioverter-defibrillator) in person programming device evaluation with iterative adjustment of the implantable device to test the function of the device and select optimal permanent programmed values with physician analysis, review and report; dual lead implantable cardioverter-defibrillator system.

In some such embodiments, the input diagnostic code is CPT code 93284: (implantable cardioverter-defibrillator) in person programming device evaluation with iterative adjustment of the implantable device to test the function of the device and select optimal permanent programmed values with physician analysis, review and report; multiple lead implantable cardioverter-defibrillator system.

In some such embodiments, the input diagnostic code is CPT code 93285: (implantable loop recorder) in person programming device evaluation with iterative adjustment of the implantable device to test the function of the device and select optimal permanent programmed values with physician analysis, review and report.

In some such embodiments, the input diagnostic code is CPT code 93288: (implantable pacemaker) in person interrogation device evaluation with physician analysis, review and report, includes connection, recording and disconnection per patient encounter; single, dual, or multiple lead pacemaker system.

In some such embodiments, the input diagnostic code is CPT code 93289: (implantable cardioverter-defibrillator) in person interrogation device evaluation (in person) with physician analysis, review and report, includes connection, recording and disconnection per patient encounter; single, dual, or multiple lead implantable cardioverter-defibrillator system, including analysis of heart rhythm derived data elements 208.

In some such embodiments, the input diagnostic code is CPT code 93290: (implantable cardiovascular monitor) in person interrogation device evaluation (in person) with physician analysis, review and report, includes connection, recording and disconnection per patient encounter; implantable cardiovascular monitor system, including analysis of 1 or more recorded physiologic cardiovascular data elements 208 from all internal and external sensors.

In some such embodiments, the input diagnostic code is representative of an ICD-10 code including but not limited to one of: I63.4x, I63.1x, and I63.9x, such as I63.4 (cerebral infarction due to embolism of cerebral arteries), I63.40 (cerebral infarction due to embolism of unspecified cerebral artery), I63.41 (cerebral infarction due to embolism of middle cerebral artery), I63.411 (cerebral infarction due to embolism of right middle cerebral artery), I63.412 (cerebral infarction due to embolism of left middle cerebral artery), I63.413 (cerebral infarction due to embolism of bilateral middle cerebral arteries), I63.419 (cerebral infarction due to embolism of unspecified middle cerebral artery), I63.42 (cerebral infarction due to embolism of anterior cerebral artery), I63.421 (cerebral infarction due to embolism of right anterior cerebral artery), I63.422 (cerebral infarction due to embolism of left anterior cerebral artery), I63.423 (cerebral infarction due to embolism of bilateral anterior cerebral arteries), I63.429 (cerebral infarction due to embolism of unspecified anterior cerebral artery), I63.43 (cerebral infarction due to embolism of posterior cerebral artery), I63.431 (cerebral infarction due to embolism of right posterior cerebral artery), I63.432 (cerebral infarction due to embolism of left posterior cerebral artery), I63.433 (cerebral infarction due to embolism of bilateral posterior cerebral arteries), I63.439 (cerebral infarction due to embolism of unspecified posterior cerebral artery), I63.44 (cerebral infarction due to embolism of cerebellar artery), I63.441 (cerebral infarction due to embolism of right cerebellar artery), I63.442 (cerebral infarction due to embolism of left cerebellar artery), I63.443 (cerebral infarction due to embolism of bilateral cerebellar arteries), I63.449 (cerebral infarction due to embolism of unspecified cerebellar artery), I63.49 (cerebral infarction due to embolism of other cerebral artery), I63.1 (cerebral infarction due to embolism of precerebral arteries), I63.10 (cerebral infarction due to embolism of unspecified precerebral artery), I63.11 (cerebral infarction due to embolism of vertebral artery), I63.111 (cerebral infarction due to embolism of right vertebral artery), I63.112 (cerebral infarction due to embolism of left vertebral artery), I63.113 (cerebral infarction due to embolism of bilateral vertebral arteries), I63.119 (cerebral infarction due to embolism of unspecified vertebral artery), I63.12 (cerebral infarction due to embolism of basilar artery), I63.13 (cerebral infarction due to embolism of carotid artery), I63.131 (cerebral infarction due to embolism of right carotid artery), I63.132 (cerebral infarction due to embolism of left carotid artery), I63.133 (cerebral infarction due to embolism of bilateral carotid arteries), I63.139 (cerebral infarction due to embolism of unspecified carotid artery), I63.19 (cerebral infarction due to embolism of other precerebral artery), I63.9 (cerebral infarction, unspecified), or an ICD-9 equivalent thereof.

In some such embodiments, the input diagnostic code is representative of an ICD-9 code including but not limited to one of: V4501 (presence of pacemaker in situ), V5331 (fitting and adjustment of cardiac pacemaker), V4502 (automatic implantable cardiac defibrillator in situ), and V5332 (fitting and adjustment of automatic implantable cardiac defibrillator).

In some such embodiments, the input diagnostic or treatment code is representative of one or more of an ICD-10 code indicative of an evaluation of congestive heart failure or risk for developing congestive heart failure including but not limited to I50.22, I50.23, I50.32, I50.42, I50.43, I50.20, and I44.7 or an ICD-9 equivalent thereof.

In some such embodiments, the input diagnostic or treatment code is representative of one or more of a CPT code indicative of an evaluation of congestive heart failure or risk for developing congestive heart failure including but not limited to 93297 and 93299.

In some such embodiments, the input data is representative of a physiologic condition that is monitored by an implanted cardiac device is indicative of a need for treatment. Examples of monitored physiologic conditions in such embodiments, include, but are not limited one or more of illness resulting in hospital readmissions, an identifying factor for risk of congestive heart failure, an abnormality in a patient's heart rate, need for frequent right ventricular pacing, alteration in electrical conduction, alteration in electromechanical synchrony, pulmonary vascular congestion, risk for thromboembolism or stroke, risk for arrhythmia, risk for syncope, risk for progressive congestive heart failure, risk for implanted device or device lead malfunction, risk for myocardial infarction, risk for vascular complications, risk for pulmonary complications, risk for complications due to diabetes, risk for complications due to hypertension, risk for renal failure, index of cardiac inotropic state, or a genotype profile that identifies risk for specific disease states.

Example 2

In this example embodiment, a method for deriving an index of compliance is provided. The index of compliance is based on one more input diagnostic and/or treatment codes that determines health care provider compliance monitoring patients with implanted cardiac devices. In such embodiments, the cardiac devices monitor patients for congestive heart failure and have wireless monitoring capability and connectivity to a monitoring network.

Example 3

In this example embodiment, a method for deriving an index of compliance is provided. The index of compliance is based on one or more of input diagnostic and/or treatment codes that determines health care provider compliance monitoring patients with implanted cardiac devices. In this example, the cardiac devices monitor heart rhythm disturbances and have wireless monitoring capability and connectivity to a monitoring network.

Example 4

In this example embodiment, a method for deriving an index of compliance is provided. The index of compliance is based on one or more input diagnostic and/or treatment codes that determines health care provider compliance monitoring patients with implanted cardiac devices. In this example, the cardiac devices monitor the functionality of the implanted system and have wireless monitoring capability and connectivity to a monitoring network.

Example 5

In this example embodiment, a method for deriving an index of compliance is provided. The index of compliance is based on one or more input diagnostic and/or treatment codes that determine health care provider compliance monitoring patients with implanted cardiac devices. In this example, the cardiac devices monitor conditions of the patient and/or implanted device and have wireless monitoring capability and connectivity to a monitoring network. Further, the health care provider includes, but is not limited to, one or more of a patient, a physician, a clinician, a cardiac device company, a physician practice, a hospital, a health care insurance company, a governmental body, or a hospital network.

Example 6

In this example, a method for deriving an index of compliance is provided. The index of compliance is based on one or more of an input diagnostic code, a treatment code and/or an identifier of hospital readmission. The index of compliance determines health care provider compliance monitoring patients with implanted cardiac devices. The cardiac devices monitor conditions of the patient and/or implanted device and have wireless monitoring capability and connectivity to a monitoring network. In this example, the health care provider includes, but is not limited to, one or more of a patient, a physician, a clinician, a cardiac device company, a physician practice, a hospital, a health care insurance company, a governmental body, and a hospital network.

Example 7

In this example, a method for monitoring a compliance index related to monitoring of an implanted cardiac device and a health care provider notification system is provided. The health care provider notification system notifies health care providers of deficiencies in compliance due to one or more of patient non-adherence to recommended treatment, a break in communication between a patient's implanted device and remote monitoring service, physician non-compliance, inadequate supervision of health care providers' monitoring system, short-comings in the entry of billing codes for remote cardiac device remote monitoring services, or ineffective delivery of standard of care treatment based on data provided by the remote monitoring system.

Example 8

In this example, a method for deriving an index of compliance is provided. The index of compliance is based on one or more of an input diagnostic code, treatment code, and/or prescribed medication regimen. The index of compliance represents health care provider compliance with one or more of routine monitoring of the condition of patients with implanted cardiac devices, where the cardiac devices have wireless monitoring capability and connectivity to a monitoring network, routine monitoring of the functionality of the implanted device, or prescribing standard of care medications to patients with certain disease states. In some embodiments, the standard of care medications or treatment include but are not limited to one or more of beta blockers, lipid lowering therapies, angiotensin converting enzyme inhibitors, angiotensin receptor blockers, aldosterone receptor blockers, hydralazine, nitrates, PCSK9 inhibitors, negative chronotropic agent, hyperpolarization-activated cyclic nucleotide-gated channel blocker, anti-platelet agent, anti-coagulant, cardiac sinus node inhibitor, respiratory support apparatus, continuous positive airway pressure device, and non-invasive ventilation therapy.

Example 9

In this example, a method for communicating a compliance index to health care providers at recurring time intervals is provided. Further, periodic monitoring of levels of compliance is provided. In this example routine monitoring of the condition of patients with implanted cardiac devices is provided, where the cardiac devices have wireless monitoring capability and connectivity to a monitoring network. Further, routine monitoring of the functionality of the implanted devices is provided. Further, the monitoring of prescribing standard of care medications to patients with certain disease states is provided.

Example 10

In this example, a method for deriving an index of compliance is provided The index of compliance is based on an input diagnostic or treatment code so as to determine health care provider compliance in delivery of care to patients. In some embodiments, recommended diagnostic tests are performed, recommended procedures are performed, or therapies are delivered with consensus based indications in specific patient sub-groups, and proper billing for services is provided.

Example 11

In this example, compliance system implementing a method for monitoring compliance of delivery of standard of care health care is provided. This is accomplished, at least in part, by using wireless data transmission and universal/standard formatting, where information is presented to relevant parties via a simple graphical user interface. The method inputs one or more data sets into the compliance system including, but not limited to, data derived from electronic medical records, billing information, pharmaceutical information, patient entered information, health care provider input, and governing bodies that determine standard of care. The method utilizes an algorithm of compliance based upon the imputed data. Relevant measured data is outputted at specific recurring time intervals to relevant parties so as to improve patient outcome. Context management is applied to facilitate data transmission, interface disparate applications, and provide feedback to the relevant parties in real time.

Example 12

In this example, a compliance system implementing a method for monitoring compliance of delivery of standard of care health care is provided, at least in part, by using wireless data transmission and universal/standard formatting, where information is presented to relevant parties via a simple graphical user interface. Input of one or more data sets into the compliance system is performed by the method. The one or more data sets include, but are not limited to, data derived from electronic medical records, billing information, pharmaceutical information, patient entered information, health care provider input, governing bodies that determine standard of care. The method implements a process that utilizes an algorithm of compliance using the inputted data. The method outputs relevant measured data at specific time intervals to relevant parties so as to improve patient outcome. The specific time intervals are determined based on an individual provider's prior history of compliance.

Example 13

In this example, a method for monitoring compliance of delivery of standard of care health care is provided, at least in part, using wireless data transmission and universal/ standard formatting, where information is presented to relevant parties via a simple graphical user interface. The method comprises inputting one or more data sets into a compliance system at determined time intervals. The data includes, but is not limited to, data derived from electronic medical records, billing information, pharmaceutical information, patient entered information, demographic data, health care provider input, and governing bodies that determine standard of care. The time intervals are based on a derived compliance index and/or an index measure of meaningful use that considers compliance data and increases the frequency of data acquisition and output of compliance index data as needed to improve standard of care health care.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1-3, 5-8, and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A computer system for determining health care provider monitoring compliance, the computer system comprising one or more processors and a memory, the memory comprising non-transitory instructions which, when executed by the one or more processors, perform a method comprising:
   A) performing a first autonomous process wherein, for each respective data element in a plurality of data elements, for each respective subject in a first plurality of subjects, the first autonomous process comprises:
      (i) measuring the respective data element in the plurality of data elements from a corresponding wireless signal transmitted by a corresponding cardiac implantable electronic medical device implanted within a corresponding subject in the first plurality of subjects, wherein the respective data element comprises (a) a corresponding medical device identifier and (b) a condition of the cardiac implantable electronic medical device or a medical device measurement,
      (ii) interrogating the respective data element to (a) determine the condition of the corresponding cardiac implantable electronic medical device or to determine the condition of the corresponding subject and (b) the identity of the corresponding subject, and
      (iii) recording, responsive to the interrogating (ii), (a) a corresponding first medical code that indicates that the condition of the corresponding cardiac implantable electronic medical device or the condition of the corresponding subject has been evaluated and (b) an associated timestamp for the interrogating in a medical record associated with the corresponding subject;
   B) performing a second autonomous process at each respective epoch in a plurality of epochs, wherein a length of each respective epoch in the plurality of epochs is set by an epoch period, the second autonomous process comprising, for each respective subject in a second plurality of subjects:
      (i) determining whether the first medical code has been recorded in the medical record associated with the respective subject during the respective epoch by parsing the medical record for the first medical code and, when found in the medical record, using the associated timestamp to determine if the first medical code is associated with the respective epoch,
      (ii) advancing a compliance counter when the medical record associated with the respective subject includes the first medical code associated with the respective epoch, and
      (iii) advancing a noncompliance counter when the medical record associated with the respective subject does not include the first medical code associated with the respective epoch, wherein,
   the first plurality of subjects constitutes all or a portion of the second plurality of subjects and wherein each subject in the second plurality of subjects has a corresponding cardiac implantable electronic medical device;
   C) comparing a compliance for the second plurality of subjects to a compliance threshold and shortening the length of the epoch period when the compliance for the second plurality of subjects does not satisfy the compliance threshold, wherein the compliance for the second plurality of subjects is based on the compliance counter or the noncompliance counter; and D) performing a third process, wherein the third process comprises:
(i) providing compliance information in accordance with the compliance counter or noncompliance counter for the second plurality of subjects, and
(ii) providing a list of subjects wherein the list of subjects is identified from the second plurality of subjects on the basis that they (a) share one or more characteristics and (b) the medical records of the subjects indicate they lack a specific therapy or a treatment that is a standard of care for subjects having the one or more characteristics.

2. The computer system of claim 1, wherein the cardiac implantable electronic device is a permanent pacemaker, an implantable cardioverter defibrillator, a cardiac resynchronization therapy device, a monitor of congestive heart failure, or an implantable loop recorder.

3. The computer system of claim 1, wherein the interrogating the data element in the first autonomous process determines the condition of the corresponding subject selected from the group consisting of a pulmonary artery pressure, an intra-thoracic impedance, an atrial arrhythmia, a ventricular arrhythmia, measurement of cardiorespiratory structure/function, an index of congestive heart failure, and a pulmonary vascular congestion.

4. The computer system of claim 1, wherein the interrogating the data element in the first autonomous process determines the condition of the corresponding subject, wherein the condition is an index of cardiorespiratory function.

5. The computer system of claim 4, wherein the condition is hyperlipidemia, thoracic impedance indices of pulmonary vascular congestion, a mean heart rate, or a cardiac inotropic state.

6. The computer system of claim 1, wherein the first medical code is an ICD-9 code, an ICD-10 code, a Current Procedure Terminology (CPT) code, or an equivalent thereof.

7. The computer system of claim 1, wherein the first medical code is extracted from the context of the cardiac implantable electronic medical record thereby providing semantic interoperability without specific reliance on a coding standard.

8. The computer system of claim 1, wherein
the interrogating the data element in the first autonomous process determines the condition of the corresponding subject, wherein the condition is an index of cardiorespiratory function, and
each respective epoch in the plurality of epochs is a day.

9. The computer system of claim 1, wherein each respective epoch in the plurality of epochs is the same length of time, and wherein the length of time is an hour or less, a day or less, two days or less, a week or less, a month or less, or a quarter of a year or less.

10. The computer system of claim 1, wherein the corresponding cardiac implantable electronic medical device connected to the corresponding subject wirelessly transmits the respective data element.

11. The computer system of claim 1, wherein
the interrogating the data element in the first autonomous process determines the condition of the corresponding subject,
the first autonomous process further comprises generating an alert for the corresponding subject when determination of the condition in the corresponding subject triggers an alert rule, and
a nature of the alert is specified by the alert rule.

12. The computer system of claim 11, wherein the condition is one or more index of cardiorespiratory function.

13. The computer system of claim 1, wherein the medical record is an electronic medical record.

14. The computer system of claim 1, wherein the first autonomous process and the second autonomous process occur concurrently.

15. The computer system of claim 1, wherein the first autonomous process, the second autonomous process, and the third process occur concurrently.

16. The computer system of claim 1, wherein the second plurality of subjects is associated with a physician, a provider group, a hospital, a hospital network, a health insurance company, a pharmacy, a governmental body, or a prescribing clinician.

17. The computer system of claim 1, wherein
the second plurality of subjects is associated with a physician, a provider group, a hospital, a hospital network, a health insurance company, a pharmacy, a governmental body or a prescribing clinician,
each subject in the second plurality of subjects has a pathologic condition,
the interrogating the data element in the first autonomous process determines a condition of the cardiac implantable electronic medical device, and
the corresponding cardiac implantable electronic medical device connected to the corresponding subject wirelessly transmits the respective data element.

18. A method for determining health care provider monitoring compliance, the method comprising:
A) performing a first autonomous process wherein, for each respective data element in a plurality of data elements, for each respective subject in a first plurality of subjects, the first autonomous process comprises:
(i) measuring the respective data element in the plurality of data elements from a corresponding wireless signal transmitted by a corresponding cardiac implantable electronic medical device implanted within a corresponding subject in the first plurality of subjects, wherein the respective data element comprises (a) a corresponding medical device identifier and (b) a condition of the cardiac implantable electronic medical device or a medical device measurement, and wherein the first plurality of subjects comprises 200 or more subjects,
(ii) interrogating the respective data element to (a) determine the condition of the corresponding cardiac implantable medical device or to determine the condition of the corresponding subject and (b) the identity of the corresponding subject, and
(iii) recording, responsive to the interrogating (ii), (a) a corresponding first medical code that indicates that the condition of the corresponding cardiac implantable electronic medical device or the condition of the corresponding subject has been evaluated and (b) an associated timestamp for the interrogating in a medical record associated with the corresponding subject;
B) performing a second autonomous process at each respective epoch in a plurality of epochs, wherein a length of each respective epoch in the plurality of epochs is set by an epoch period, the second autonomous process comprising, for each respective subject in a second plurality of subjects:
- (i) determining whether the first medical code has been recorded in the medical record associated with the respective subject during the respective epoch by parsing the medical record for the first medical code and, when found in the medical record, using the associated timestamp to determine if the first medical code is associated with respective epoch,
- (ii) advancing a compliance counter when the medical record associated with the respective subject includes the first medical code associated with the respective epoch, and
- (iii) advancing a noncompliance counter when the medical record associated with the respective subject does not include the first medical code associated with the respective epoch, wherein, the first plurality of subjects constitutes all or a portion of the second plurality of subjects and wherein each subject in the second plurality of subjects has a corresponding cardiac implantable electronic medical device;

C) comparing a compliance for the second plurality of subjects to a compliance threshold and shortening the length of the epoch period when the compliance for the second plurality of subjects does not satisfy the compliance threshold, wherein the compliance for the second plurality of subjects is based on the compliance counter or the noncompliance counter; and D) performing a third process, wherein the third process comprises:
- (i) providing compliance information in accordance with the compliance counter or noncompliance counter for the second plurality of subjects, and
- (ii) providing a list of subjects wherein the list of subjects is identified from the second plurality of subjects on the basis that they (a) share one or more characteristics and (b) the medical records of the subjects indicate they lack a specific therapy or a treatment that is a standard of care for subjects having the one or more characteristics.

19. A non-transitory computer readable storage medium, wherein the non-transitory computer readable storage medium stores instructions, which when executed by a computer system, cause the computer system to perform a method for determining health care provider monitoring compliance, the method comprising:

A) performing a first autonomous process wherein, for each respective data element in a plurality of data elements, for each respective subject in a first plurality of subjects, the first autonomous process comprises:
- (i) measuring the respective data element in the plurality of data elements from a corresponding wireless signal transmitted by a corresponding cardiac implantable electronic medical device implanted within a corresponding subject in the first plurality of subjects, wherein the respective data element comprises (a) a corresponding medical device identifier and (b) a condition of the cardiac implantable electronic medical device or a medical device measurement,
- (ii) interrogating the respective data element to (a) determine the condition of the corresponding cardiac implantable electronic medical device or to determine the condition of the corresponding subject and (b) the identity of the corresponding subject, and
- (iii) recording, responsive to the interrogating (ii), (a) a corresponding first medical code that indicates that the condition of the corresponding cardiac implantable electronic medical device or the condition of the corresponding subject has been evaluated and (b) an associated timestamp for the interrogating in a medical record associated with the corresponding subject;

B) performing a second autonomous process at each respective epoch in a plurality of epochs, wherein a length of each respective epoch in the plurality of epochs is set by an epoch period, the second autonomous process comprising, for each respective subject in a second plurality of subjects:
- (i) determining whether the first medical code has been recorded in the medical record associated with the respective subject during the respective epoch by parsing the medical record for the first medical code and, when found in the medical record, using the associated timestamp to determine if the first medical code is associated with respective epoch,
- (ii) advancing a compliance counter when the medical record associated with the respective subject includes the first medical code associated with the respective epoch, and
- (iii) advancing a noncompliance counter when the medical record associated with the respective subject does not include the first medical code associated with the respective epoch, wherein, the first plurality of subjects constitutes all or a portion of the second plurality of subjects and wherein each subject in the second plurality of subjects has a corresponding medical device;

C) comparing a compliance for the second plurality of subjects to a compliance threshold and shortening the length of the epoch period when the compliance for the second plurality of subjects does not satisfy the compliance threshold, wherein the compliance for the second plurality of subjects is based on the compliance counter or the noncompliance counter; and D) performing a third process, wherein the third process comprises:
- (i) providing compliance information in accordance with the compliance counter or the noncompliance counter for the second plurality of subjects, and
- (ii) providing a list of subjects wherein the list of subjects is identified from the second plurality of subjects on the basis that they (a) share one or more characteristics and (b) the medical records of the subjects indicate they lack a specific therapy or a treatment that is standard of care for subjects having the one or more characteristics.

20. The method of claim 1, wherein the providing the compliance information in accordance with the compliance counter or the noncompliance counter is responsive to receiving a compliance request.

21. The method of claim 1, wherein the third autonomous process further comprises providing one or more suggested treatment options based upon the compliance information in accordance with the compliance counter or the noncompliance counter.

22. The method of claim 1, wherein:
the first plurality of subjects comprises 200 or more subjects; and
the second plurality of subjects comprises 200 or more subjects.

23. The method of claim 1, further comprising performing, for each respective subject in the list of subjects, a diagnostic test on the cardiac implantable electronic medical device corresponding to the respective subject.

24. A computer system for determining health care provider monitoring compliance, the computer system comprising one or more processors and a memory, the memory comprising non-transitory instructions which, when executed by the one or more processors, perform a method comprising:
- A) performing a first autonomous process wherein, for each respective data element in a plurality of data elements, for each respective subject in a first plurality of subjects, the first autonomous process comprises:
  - (i) measuring the respective data element in the plurality of data elements from a corresponding wireless signal transmitted by a corresponding cardiac implantable electronic medical device implanted within a corresponding subject in the first plurality of subjects, wherein the respective data element comprises (a) a corresponding medical device identifier and (b) a condition of the cardiac implantable electronic medical device or a medical device measurement,
  - (ii) interrogating the respective data element to (a) determine the condition of the corresponding cardiac implantable electronic medical device or to determine the condition of the corresponding subject and (b) the identity of the corresponding subject, and
  - (iii) recording, responsive to the interrogating (ii), (a) a corresponding first medical code that indicates that the condition of the corresponding cardiac implantable electronic medical device or the condition of the corresponding subject has been evaluated and (b) an associated timestamp for the interrogating in a medical record associated with the corresponding subject;
- B) performing a second autonomous process at each respective epoch in a plurality of epochs, the second autonomous process comprising, for each respective subject in a second plurality of subjects:
  - (i) determining whether the first medical code has been recorded in the medical record associated with the respective subject during the respective epoch by parsing the medical record for the first medical code and, when found in the medical record, using the associated timestamp to determine if the first medical code is associated with the respective epoch,
  - (ii) advancing a compliance counter when the medical record associated with the respective subject includes the first medical code associated with the respective epoch, and
  - (iii) advancing a noncompliance counter when the medical record associated with the respective subject does not include the first medical code associated with the respective epoch, wherein,
- the first plurality of subjects constitutes all or a portion of the second plurality of subjects and wherein each subject in the second plurality of subjects has a corresponding cardiac implantable electronic medical device;
- C) performing a third process, wherein the third process comprises:
  - (i) providing compliance information in accordance with the compliance counter or noncompliance counter for the second plurality of subjects, and
  - (ii) providing a list of subjects wherein the list of subjects is identified from the second plurality of subjects on the basis that they (a) share one or more characteristics and (b) the medical records of the subjects indicate they lack a specific therapy or a treatment that is a standard of care for subjects having the one or more characteristics; and
  - D) performing, for each respective subject in the list of subjects, a diagnostic test on the cardiac implantable electronic medical device corresponding to the respective subject.

25. The computer system of claim 24, wherein the cardiac implantable electronic device is a permanent pacemaker, an implantable cardioverter defibrillator, a cardiac resynchronization therapy device, a monitor of congestive heart failure, or an implantable loop recorder.

26. The computer system of claim 24, wherein the interrogating the data element in the first autonomous process determines the condition of the corresponding subject selected from the group consisting of a pulmonary artery pressure, an intra-thoracic impedance, an atrial arrhythmia, a ventricular arrhythmia, measurement of cardiorespiratory structure/function, an index of congestive heart failure, and a pulmonary vascular congestion.

27. The computer system of claim 24, wherein the interrogating the data element in the first autonomous process determines the condition of the corresponding subject, wherein the condition is an index of cardiorespiratory function.

28. The computer system of claim 27, wherein the condition is hyperlipidemia, thoracic impedance indices of pulmonary vascular congestion, a mean heart rate, or a cardiac inotropic state.

29. The computer system of claim 24, wherein the first medical code is an ICD-9 code, an ICD-10 code, a Current Procedure Terminology (CPT) code, or an equivalent thereof.

30. The computer system of claim 24, wherein the first medical code is extracted from the context of the cardiac implantable electronic medical record thereby providing semantic interoperability without specific reliance on a coding standard.

31. The computer system of claim 24, wherein
the interrogating the data element in the first autonomous process determines the condition of the corresponding subject, wherein the condition is an index of cardiorespiratory function, and
each respective epoch in the plurality of epochs is a day.

32. The computer system of claim 24, wherein each respective epoch in the plurality of epochs is the same length of time, and wherein the length of time is an hour or less, a day or less, two days or less, a week or less, a month or less, or a quarter of a year or less.

33. The computer system of claim 24, wherein the corresponding cardiac implantable electronic medical device connected to the corresponding subject wirelessly transmits the respective data element.

34. The computer system of claim 24, wherein
the interrogating the data element in the first autonomous process determines the condition of the corresponding subject,
the first autonomous process further comprises generating an alert for the corresponding subject when determination of the condition in the corresponding subject triggers an alert rule, and
a nature of the alert is specified by the alert rule.

35. The computer system of claim 34, wherein the condition is one or more index of cardiorespiratory function.

36. The computer system of claim 24, wherein the medical record is an electronic medical record.

37. The computer system of claim 24, wherein the first autonomous process and the second autonomous process occur concurrently.

38. The computer system of claim 24, wherein the first autonomous process, the second autonomous process, and the third process occur concurrently.

39. The computer system of claim 24, wherein the second plurality of subjects is associated with a physician, a provider group, a hospital, a hospital network, a health insurance company, a pharmacy, a governmental body, or a prescribing clinician.

40. The computer system of claim 24, wherein
the second plurality of subjects is associated with a physician, a provider group, a hospital, a hospital network, a health insurance company, a pharmacy, a governmental body or a prescribing clinician,
each subject in the second plurality of subjects has a pathologic condition,
the interrogating the data element in the first autonomous process determines a condition of the cardiac implantable electronic medical device, and
the corresponding cardiac implantable electronic medical device connected to the corresponding subject wirelessly transmits the respective data element.

41. The method of claim 24, wherein the providing the compliance information in accordance with the compliance counter or the noncompliance counter is responsive to receiving a compliance request.

42. The method of claim 24, wherein the third autonomous process further comprises providing one or more suggested treatment options based upon the compliance information in accordance with the compliance counter or the noncompliance counter.

43. The method of claim 24, wherein:
the first plurality of subjects comprises 200 or more subjects; and
the second plurality of subjects comprises 200 or more subjects.

44. A method for determining health care provider monitoring compliance, the method comprising:
A) performing a first autonomous process wherein, for each respective data element in a plurality of data elements, for each respective subject in a first plurality of subjects, the first autonomous process comprises:
(i) measuring the respective data element in the plurality of data elements from a corresponding wireless signal transmitted by a corresponding cardiac implantable electronic medical device implanted within a corresponding subject in the first plurality of subjects, wherein the respective data element comprises (a) a corresponding medical device identifier and (b) a condition of the cardiac implantable electronic medical device or a medical device measurement,
(ii) interrogating the respective data element to (a) determine the condition of the corresponding cardiac implantable electronic medical device or to determine the condition of the corresponding subject and (b) the identity of the corresponding subject, and
(iii) recording, responsive to the interrogating (ii), (a) a corresponding first medical code that indicates that the condition of the corresponding cardiac implantable electronic medical device or the condition of the corresponding subject has been evaluated and (b) an associated timestamp for the interrogating in a medical record associated with the corresponding subject;

B) performing a second autonomous process at each respective epoch in a plurality of epochs, the second autonomous process comprising, for each respective subject in a second plurality of subjects:
(i) determining whether the first medical code has been recorded in the medical record associated with the respective subject during the respective epoch by parsing the medical record for the first medical code and, when found in the medical record, using the associated timestamp to determine if the first medical code is associated with the respective epoch,
(ii) advancing a compliance counter when the medical record associated with the respective subject includes the first medical code associated with the respective epoch, and
(iii) advancing a noncompliance counter when the medical record associated with the respective subject does not include the first medical code associated with the respective epoch, wherein,
the first plurality of subjects constitutes all or a portion of the second plurality of subjects and wherein each subject in the second plurality of subjects has a corresponding cardiac implantable electronic medical device;
C) performing a third process, wherein the third process comprises:
(i) providing compliance information in accordance with the compliance counter or noncompliance counter for the second plurality of subjects, and
(ii) providing a list of subjects wherein the list of subjects is identified from the second plurality of subjects on the basis that they (a) share one or more characteristics and (b) the medical records of the subjects indicate they lack a specific therapy or a treatment that is a standard of care for subjects having the one or more characteristics; and
D) performing, for each respective subject in the list of subjects, a diagnostic test on the cardiac implantable electronic medical device corresponding to the respective subject.

45. A non-transitory computer readable storage medium, wherein the non-transitory computer readable storage medium stores instructions, which when executed by a computer system, cause the computer system to perform a method for determining health care provider monitoring compliance, the method comprising:
A) performing a first autonomous process wherein, for each respective data element in a plurality of data elements, for each respective subject in a first plurality of subjects, the first autonomous process comprises:
(i) measuring the respective data element in the plurality of data elements from a corresponding wireless signal transmitted by a corresponding cardiac implantable electronic medical device implanted within a corresponding subject in the first plurality of subjects, wherein the respective data element comprises (a) a corresponding medical device identifier and (b) a condition of the cardiac implantable electronic medical device or a medical device measurement,
(ii) interrogating the respective data element to (a) determine the condition of the corresponding cardiac implantable electronic medical device or to determine the condition of the corresponding subject and (b) the identity of the corresponding subject, and
(iii) recording, responsive to the interrogating (ii), (a) a corresponding first medical code that indicates that the condition of the corresponding cardiac implantable electronic medical device or the condition of the corresponding subject has been evaluated and (b) an associated timestamp for the interrogating in a medical record associated with the corresponding subject;

B) performing a second autonomous process at each respective epoch in a plurality of epochs, the second autonomous process comprising, for each respective subject in a second plurality of subjects:
   (i) determining whether the first medical code has been recorded in the medical record associated with the respective subject during the respective epoch by parsing the medical record for the first medical code and, when found in the medical record, using the associated timestamp to determine if the first medical code is associated with the respective epoch,
   (ii) advancing a compliance counter when the medical record associated with the respective subject includes the first medical code associated with the respective epoch, and
   (iii) advancing a noncompliance counter when the medical record associated with the respective subject does not include the first medical code associated with the respective epoch, wherein, the first plurality of subjects constitutes all or a portion of the second plurality of subjects and wherein each subject in the second plurality of subjects has a corresponding cardiac implantable electronic medical device;

C) performing a third process, wherein the third process comprises:
   (i) providing compliance information in accordance with the compliance counter or noncompliance counter for the second plurality of subjects, and
   (ii) providing a list of subjects wherein the list of subjects is identified from the second plurality of subjects on the basis that they (a) share one or more characteristics and (b) the medical records of the subjects indicate they lack a specific therapy or a treatment that is a standard of care for subjects having the one or more characteristics; and D) performing, for each respective subject in the list of subjects, a diagnostic test on the cardiac implantable electronic medical device corresponding to the respective subject.

* * * * *